(12) United States Patent
Tieck et al.

(10) Patent No.: US 10,124,113 B2
(45) Date of Patent: Nov. 13, 2018

(54) DETECTING CONDITIONS ASSOCIATED WITH MEDICAL DEVICE OPERATIONS USING MATCHED FILTERS

(71) Applicant: MEDTRONIC MINIMED, INC., Northridge, CA (US)

(72) Inventors: R. Marie Tieck, Los Angeles, CA (US); Juan M. Alderete, Jr., Granada Hills, CA (US); Matthew I. Haller, Valley Village, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 15 days.

(21) Appl. No.: 15/192,877

(22) Filed: Jun. 24, 2016

(65) Prior Publication Data

US 2016/0303319 A1    Oct. 20, 2016

Related U.S. Application Data

(62) Division of application No. 13/966,183, filed on Aug. 13, 2013, now Pat. No. 9,402,949.

(51) Int. Cl.
*A61M 5/168* (2006.01)
*A61M 5/142* (2006.01)
*A61M 5/145* (2006.01)

(52) U.S. Cl.
CPC ...... *A61M 5/16831* (2013.01); *A61M 5/1452* (2013.01); *A61M 5/14216* (2013.01);
(Continued)

(58) Field of Classification Search
CPC .......... A61M 5/16831; A61M 5/14248; A61M 5/1452; A61M 5/14216;
(Continued)

(56) References Cited

U.S. PATENT DOCUMENTS 3,631,847 A    1/1972  Hobbs, II
4,212,738 A    7/1980  Henne
(Continued)

FOREIGN PATENT DOCUMENTS

DE    4329229    3/1995
EP    0319268    11/1988
(Continued)

OTHER PUBLICATIONS

Doron Levy, "Introduction to Numerical Analysis", dated Sep. 21, 2010 and available on line Jan. 2, 2018 at http://www2.math.umd.edu/~dlevy/books/na.pdf.*

(Continued)

*Primary Examiner* — Amber Stiles
(74) *Attorney, Agent, or Firm* — Lorenz & Kopf, LLP

(57) ABSTRACT

Apparatus are provided for infusion devices and related operating methods. An exemplary device includes a sensing arrangement to provide an output indicative of a characteristic that is influenced by operation of the device, and a control module that is coupled to the sensing arrangement to apply a matched filter corresponding to a condition associated with the operation of the device to the output of the sensing arrangement and detect that condition based on the filtered output. In one example, the device includes a motor coupled to a plunger of a reservoir and operable to displace the plunger, wherein the characteristic is a force opposing displacement of the plunger and the control module detects an occlusion condition in a fluid path from the reservoir based on filtered force measurements.

18 Claims, 14 Drawing Sheets

(52) U.S. Cl.
CPC ............... *A61M 5/14248* (2013.01); *A61M 2005/16863* (2013.01); *A61M 2205/332* (2013.01); *A61M 2205/3303* (2013.01); *A61M 2205/3306* (2013.01); *A61M 2205/3317* (2013.01); *A61M 2205/3584* (2013.01); *A61M 2205/50* (2013.01); *A61M 2230/201* (2013.01)

(58) Field of Classification Search
CPC .... A61M 2205/3303; A61M 2230/201; A61M 2205/50; A61M 2005/16863; A61M 2205/3584; A61M 2205/332; A61M 2205/3317; A61M 2205/3306
See application file for complete search history.

(56) References Cited

U.S. PATENT DOCUMENTS

| | | | |
|---|---|---|---|
| 4,270,532 A | 6/1981 | Franetzki et al. | |
| 4,282,872 A | 8/1981 | Franetzki et al. | |
| 4,373,527 A | 2/1983 | Fischell | |
| 4,395,259 A | 7/1983 | Prestele et al. | |
| 4,433,072 A | 2/1984 | Pusineri et al. | |
| 4,443,218 A | 4/1984 | Decant, Jr. et al. | |
| 4,494,950 A | 1/1985 | Fischell | |
| 4,542,532 A | 9/1985 | McQuilkin | |
| 4,550,731 A | 11/1985 | Batina et al. | |
| 4,559,037 A | 12/1985 | Franetzki et al. | |
| 4,562,751 A | 1/1986 | Nason et al. | |
| 4,671,288 A | 6/1987 | Gough | |
| 4,678,408 A | 7/1987 | Nason et al. | |
| 4,685,903 A | 8/1987 | Cable et al. | |
| 4,731,051 A | 3/1988 | Fischell | |
| 4,731,726 A | 3/1988 | Allen, III | |
| 4,781,798 A | 11/1988 | Gough | |
| 4,803,625 A | 2/1989 | Fu et al. | |
| 4,809,697 A | 3/1989 | Causey, III et al. | |
| 4,826,810 A | 5/1989 | Aoki | |
| 4,871,351 A | 10/1989 | Feingold | |
| 4,898,578 A | 2/1990 | Rubalcaba, Jr. | |
| 5,003,298 A | 3/1991 | Havel | |
| 5,011,468 A | 4/1991 | Lundquist et al. | |
| 5,019,974 A | 5/1991 | Beckers | |
| 5,050,612 A | 9/1991 | Matsumura | |
| 5,078,683 A | 1/1992 | Sancoff et al. | |
| 5,080,653 A | 1/1992 | Voss et al. | |
| 5,097,122 A | 3/1992 | Colman et al. | |
| 5,100,380 A | 3/1992 | Epstein et al. | |
| 5,101,814 A | 4/1992 | Palti | |
| 5,108,819 A | 4/1992 | Heller et al. | |
| 5,153,827 A | 10/1992 | Coutre et al. | |
| 5,165,407 A | 11/1992 | Wilson et al. | |
| 5,178,603 A * | 1/1993 | Prince ............... | A61M 1/30 604/6.01 |
| 5,247,434 A | 9/1993 | Peterson et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,284,140 A | 2/1994 | Allen et al. | |
| 5,299,571 A | 4/1994 | Mastrototaro | |
| 5,307,263 A | 4/1994 | Brown | |
| 5,317,506 A | 5/1994 | Coutre et al. | |
| 5,320,725 A | 6/1994 | Gregg et al. | |
| 5,322,063 A | 6/1994 | Allen et al. | |
| 5,338,157 A | 8/1994 | Blomquist | |
| 5,339,821 A | 8/1994 | Fujimoto | |
| 5,341,291 A | 8/1994 | Roizen et al. | |
| 5,350,411 A | 9/1994 | Ryan et al. | |
| 5,356,786 A | 10/1994 | Heller et al. | |
| 5,357,427 A | 10/1994 | Langen et al. | |
| 5,368,562 A | 11/1994 | Blomquist et al. | |
| 5,370,622 A | 12/1994 | Livingston et al. | |
| 5,371,687 A | 12/1994 | Holmes, II et al. | |
| 5,376,070 A | 12/1994 | Purvis et al. | |
| 5,390,671 A | 2/1995 | Lord et al. | |
| 5,391,250 A | 2/1995 | Cheney, II et al. | |
| 5,403,700 A | 4/1995 | Heller et al. | |
| 5,411,647 A | 5/1995 | Johnson et al. | |
| 5,482,473 A | 1/1996 | Lord et al. | |
| 5,485,408 A | 1/1996 | Blomquist | |
| 5,505,709 A | 4/1996 | Funderburk et al. | |
| 5,497,772 A | 5/1996 | Schulman et al. | |
| 5,543,326 A | 8/1996 | Heller et al. | |
| 5,569,186 A | 10/1996 | Lord et al. | |
| 5,569,187 A | 10/1996 | Kaiser | |
| 5,573,506 A | 11/1996 | Vasko | |
| 5,582,593 A | 12/1996 | Hultman | |
| 5,586,553 A | 12/1996 | Halili et al. | |
| 5,593,390 A | 1/1997 | Castellano et al. | |
| 5,593,852 A | 1/1997 | Heller et al. | |
| 5,594,638 A | 1/1997 | Iliff | |
| 5,609,060 A | 3/1997 | Dent | |
| 5,626,144 A | 5/1997 | Tacklind et al. | |
| 5,630,710 A | 5/1997 | Tune et al. | |
| 5,643,212 A | 7/1997 | Coutre | |
| 5,660,163 A | 8/1997 | Schulman et al. | |
| 5,660,176 A | 8/1997 | Iliff | |
| 5,665,065 A | 9/1997 | Colman et al. | |
| 5,665,222 A | 9/1997 | Heller et al. | |
| 5,685,844 A | 11/1997 | Marttila | |
| 5,687,734 A | 11/1997 | Dempsey et al. | |
| 5,704,366 A | 1/1998 | Tacklind et al. | |
| 5,750,926 A | 5/1998 | Schulman et al. | |
| 5,754,111 A | 5/1998 | Garcia | |
| 5,764,159 A | 6/1998 | Neftel | |
| 5,772,635 A | 6/1998 | Dastur et al. | |
| 5,779,665 A | 7/1998 | Mastrototaro et al. | |
| 5,788,669 A | 8/1998 | Peterson | |
| 5,791,344 A | 8/1998 | Schulman et al. | |
| 5,800,420 A | 9/1998 | Gross et al. | |
| 5,807,336 A | 9/1998 | Russo et al. | |
| 5,814,015 A | 9/1998 | Gargano et al. | |
| 5,822,715 A | 10/1998 | Worthington et al. | |
| 5,832,448 A | 11/1998 | Brown | |
| 5,840,020 A | 11/1998 | Heinonen et al. | |
| 5,861,018 A | 1/1999 | Feierbach et al. | |
| 5,868,669 A | 2/1999 | Iliff | |
| 5,871,465 A | 2/1999 | Vasko | |
| 5,879,163 A | 3/1999 | Brown et al. | |
| 5,885,245 A | 3/1999 | Lynch et al. | |
| 5,897,493 A | 4/1999 | Brown | |
| 5,899,855 A | 5/1999 | Brown | |
| 5,904,708 A | 5/1999 | Goedeke | |
| 5,913,310 A | 6/1999 | Brown | |
| 5,917,346 A | 6/1999 | Gord | |
| 5,918,603 A | 7/1999 | Brown | |
| 5,925,021 A | 7/1999 | Castellano et al. | |
| 5,933,136 A | 8/1999 | Brown | |
| 5,935,099 A | 8/1999 | Peterson et al. | |
| 5,940,801 A | 8/1999 | Brown | |
| 5,956,501 A | 9/1999 | Brown | |
| 5,960,403 A | 9/1999 | Brown | |
| 5,965,380 A | 10/1999 | Heller et al. | |
| 5,972,199 A | 10/1999 | Heller et al. | |
| 5,978,236 A | 11/1999 | Faberman et al. | |
| 5,997,476 A | 12/1999 | Brown | |
| 5,999,848 A | 12/1999 | Gord et al. | |
| 5,999,849 A | 12/1999 | Gord et al. | |
| 6,009,339 A | 12/1999 | Bentsen et al. | |
| 6,032,119 A | 2/2000 | Brown et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,101,478 A | 8/2000 | Brown | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,162,611 A | 12/2000 | Heller et al. | |
| 6,175,752 B1 | 1/2001 | Say et al. | |
| 6,183,412 B1 | 2/2001 | Benkowski et al. | |

(56) References Cited

U.S. PATENT DOCUMENTS

| | | |
|---|---|---|
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,323,142 B2 | 1/2008 | Pendo et al. |
| 7,396,330 B2 | 7/2008 | Banet et al. |
| 7,402,153 B2 | 7/2008 | Steil et al. |
| 7,621,893 B2 | 11/2009 | Moberg et al. |
| 8,197,444 B1 * | 6/2012 | Bazargan ........ A61M 5/16854 604/131 |
| 8,474,332 B2 | 7/2013 | Bente, IV |
| 8,603,026 B2 | 12/2013 | Favreau |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2003/0222029 A1 * | 12/2003 | Muller ............... A61M 1/3693 210/739 |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2010/0185142 A1 | 7/2010 | Kamen et al. |
| 2011/0233393 A1 | 9/2011 | Hanson et al. |
| 2012/0160033 A1 * | 6/2012 | Kow ............... G01F 13/00 73/861.71 |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS

PCT Search Report (PCT/US02/03299), dated Oct. 31, 2002, Medtronic Minimed, Inc.

(Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting a Key to Accurate Mealtime Boluses in Intensive Diabetes Therapy. Practical Diabetology, vol. 11, No. 2; pp. 22-28.

(56) References Cited

OTHER PUBLICATIONS

Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed• Technologies.
(Intensive Diabetes Management, 1995). Insulin Infusion Pump Therapy. Pages 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON®plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.

Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intravenous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.

(56) References Cited

OTHER PUBLICATIONS

Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.
Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.
Shichiri, Motoaki, et al., "Glycaemic Control in a Pacreatectomized Dogs with a Wearable Artificial Endocrine Pancreas," Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.
Shichiri, M., et al., "Membrane design for extending the long-life of an implantable glucose sensor," Diab. Nutr. Metab., vol. 2, No. 4, 1989, pp. 309-313.
Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.
Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.
Shichiri, Motoaki, et al., "Wearable Artificial Endocrine Pancreas with Needle-Type Glucose Sensor," The Lancet, Nov. 20, 1982, pp. 1129-1131.
Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.
Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.
Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.
Sternberg, Robert, et al., "Study and Development of Multilayer Needle-type Enzyme-based Glucose Microsensors," Biosensors, vol. 4, 1988, pp. 27-40.
Tamiya, E., et al., "Micro Glucose Sensors using Electron Mediators Immobilized on a Polypyrrole-Modified Electrode," Sensors and Actuators, vol. 18, 1989, pp. 297-307.
Tsukagoshi, Kazuhiko, et al., "Specific Complexation with Mono- and Disaccharides that can be Detected by Circular Dichroism," J. Org. Chem., vol. 56, 1991, pp. 4089-4091.
Urban, G., et al., "Miniaturized multi-enzyme biosensors integrated with pH sensors on flexible polymer carriers for in vivo applciations," Biosensors & Bioelectronics, vol. 7, 1992, pp. 733-739.
Ubran, G., et al., "Miniaturized thin-film biosensors using covalently immobilized glucose oxidase," Biosensors & Bioelectronics, vol. 6, 1991, pp. 555-562.
Velho, G., et al., "In vivo calibration of a subcutaneous glucose sensor for determination of subcutaneous glucose kinetics," Diab. Nutr. Metab., vol. 3, 1988, pp. 227-233.
Wang, Joseph, et al., "Needle-Type Dual Microsensor for the Simultaneous Monitoring of Glucose and Insulin," Analytical Chemistry, vol. 73, 2001, pp. 844-847.
Yamasaki, Yoshimitsu, et al., "Direct Measurement of Whole Blood Glucose by a Needle-Type Sensor," Clinics Chimica Acta, vol. 93, 1989, pp. 93-98.
Yokoyama, K., "Integrated Biosensor for Glucose and Galactose," Analytica Chimica Acta, vol. 218, 1989, pp. 137-142.

* cited by examiner

US 10,124,113 B2

DETECTING CONDITIONS ASSOCIATED WITH MEDICAL DEVICE OPERATIONS USING MATCHED FILTERS

CROSS-REFERENCE TO RELATED APPLICATIONS

This application is a division of U.S. patent application Ser. No. 13/966,183, filed Aug. 13, 2013.

TECHNICAL FIELD

Embodiments of the subject matter described herein relate generally to medical devices, and more particularly, embodiments of the subject matter relate to detecting or otherwise identifying one or more conditions associated with operation of a medical device using matched filters.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Often, fluid infusion devices include a force sensor or some other sensing arrangement designed to detect and indicate potential non-delivery of medication to the patient due to a fluid path occlusion or some other condition within the infusion device.

In some situations, a comparison test may be utilized to identify the potential occurrence of a particular condition when a measurement value exceeds a threshold value indicative of the condition to be detected. For example, an occlusion may be detected when a measured force exceeds an occlusion force threshold. Due to noise, manufacturing variations, component tolerances, and/or other factors, the threshold value used for such comparison tests often includes a margin that accounts for such factors to achieve a desired level of accuracy and/or reliability by avoiding or otherwise limiting the frequency and/or amount of false positives that could otherwise be caused by those factors. However, including a margin in a threshold value may delay response time and/or limit the ability to detect incipient conditions. Accordingly, it is desirable to provide a means for detecting conditions associated with operation of an infusion pump device as accurately and reliably as possible with the least amount of delay.

BRIEF SUMMARY

An embodiment of an electronic device, such as an infusion device or another portable medical device, is provided. The device includes a sensing arrangement to provide an output indicative of a characteristic that is influenced by operation of the device, and a control module that is coupled to the sensing arrangement to apply a matched filter corresponding to a condition associated with the operation of the device to the output of the sensing arrangement and detect that condition based on the filtered output.

In one embodiment, a fluid infusion device includes a motor operable to displace a plunger of a reservoir, a sensing arrangement to provide an output indicative of a characteristic influenced by displacement of the plunger, and a control module coupled to the sensing arrangement to apply a matched filter to the output of the sensing arrangement and detect a condition corresponding to the matched filter based on the filtered output.

In another embodiment, a method is provided for detecting a condition associated with operation of a device. The method involves obtaining an output indicative of a characteristic influenced by the operation of the device from a sensing arrangement, applying a matched filter corresponding to the condition of interest to the output of the sensing arrangement, and detecting the condition based on the filtered output.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and not necessarily drawn to scale.

DETAILED DESCRIPTION

Figure 1:
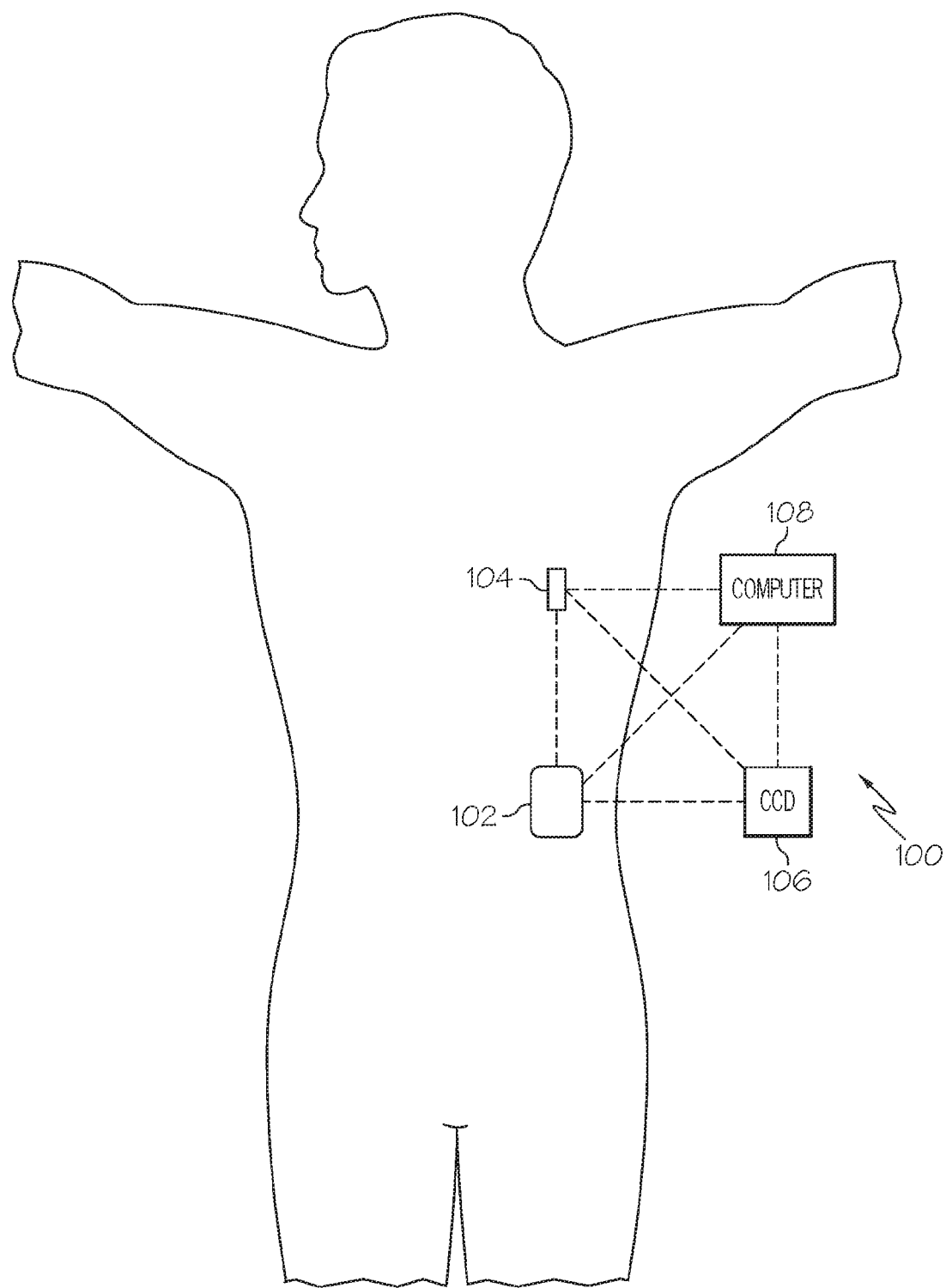
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented with any electronic device to detect any particular condition associated with or otherwise influenced by operation of the device, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail herein. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893, which are herein incorporated by reference. That said, the subject matter described herein is not limited to infusion devices and may be implemented in an equivalent manner for any medical device or other electronic device capable of exhibiting any particular condition of interest to be detected.

Embodiments of the subject matter described herein generally relate to infusion devices that utilize matched filters to detect or otherwise identify a particular condition of interest associated with operation of the infusion device, such as, for example, an occlusion condition in a fluid path, a leakage condition in a fluid path, or the like. As used herein, an occlusion condition should be understood as referring to a condition in which delivery of fluid along a fluid path is impaired by an obstruction or impediment along the fluid path, while a leakage condition should be understood as referring to a condition in which delivery of fluid along a fluid path is impaired by a loss of fluid (or pressure) caused by a degraded seal or a leak in a fluid reservoir or elsewhere along the fluid path. As described in greater detail below, a matched filter associated with a particular condition of interest is applied to the output of a sensing arrangement to obtain a filtered output used to detect that condition of interest. For example, a matched filter associated with an occlusion condition may be applied to the output of a force sensing arrangement to obtain a filtered force measurement utilized to detect an occlusion condition. The impulse response of the matched filter corresponds to or otherwise matches the expected (or anticipated) output of the sensing arrangement when that condition of interest exists or is otherwise exhibited by the infusion device. In other words, the expected output of the sensing arrangement provides a known signal response or template used to generate finite impulse response (FIR) filter coefficient values for the matched filter such that the impulse response of the matched filter reflects a reversed version of the expected output with respect to an analysis domain variable. For example, the impulse response of the matched filter may correspond to or otherwise match the expected (or anticipated) force that would be measured by a force sensing arrangement when an occlusion condition exists.

As will be understood, a matched filter provides relatively high signal-to-noise ratio (SNR). This, in turn, allows for relatively lower threshold values to be utilized to detect the condition of interest by reducing any margin that would otherwise be included to account for potential noise, manufacturing variations, component tolerances, and the like. Accordingly, the condition of interest to be detected earlier using lower threshold values and with improved accuracy and/or reliability by increasing SNR. Additionally, the filtered output resulting from applying the matched filter exhibits an exaggerated response to the condition of interest relative to the unfiltered output of the sensing arrangement, which further reduces the response time for detecting the condition of interest. Accordingly, incipient conditions may be detected quickly, accurately, and reliably so that appropriate remedial actions may be initiated to prevent or otherwise mitigate impact on the delivery of fluid to a user.

In accordance with one or more embodiments, a matched filter may be associated with a particular operating configuration and/or operating mode. For example, a matched filter for an occlusion condition in a fluid infusion device may be associated with a particular delivery mode (or delivery rate) that the infusion device is currently operating and/or a particular delivery configuration for the infusion device. The delivery configuration information associated with the matched filter may include, for example, identification of the particular type of infusion set and/or cannula being used with the infusion device, identification of the length and/or diameter of any tubing being used in the infusion set with the infusion device, the particular type of reservoir being used with the infusion device, the size of the reservoir (e.g., length and/or volume of the reservoir barrel), and/or identification of any other aspect of the physical configuration of the infusion device 200, 802 that is capable of influencing delivery of fluid to a user and/or the characteristic sensed by a sensing arrangement. In this regard, multiple different matched filters may be generated and maintained for use with each particular combination of delivery configuration and delivery mode. For example, a first matched filter utilized to detect an occlusion condition may be associated with a basal delivery mode (or basal delivery rate) for a particular combination of reservoir and infusion set, with a second matched filter utilized to detect an occlusion condition being associated with a bolus delivery mode for that combination of reservoir and infusion set and a third matched filter utilized to detect an occlusion condition being associated with the basal delivery mode and a different combination of reservoir and infusion set. Thus, if the delivery mode and/or the delivery configuration for an infusion device changes during operation, the appropriate matched filter for the current delivery mode and/or delivery configuration may be dynamically selected and applied, thereby enabling the detection process to adapt to changes in the operation of the infusion device substantially in real-time.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. patent application Ser. No. 13/049,803, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

As described above, in some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402, 153, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
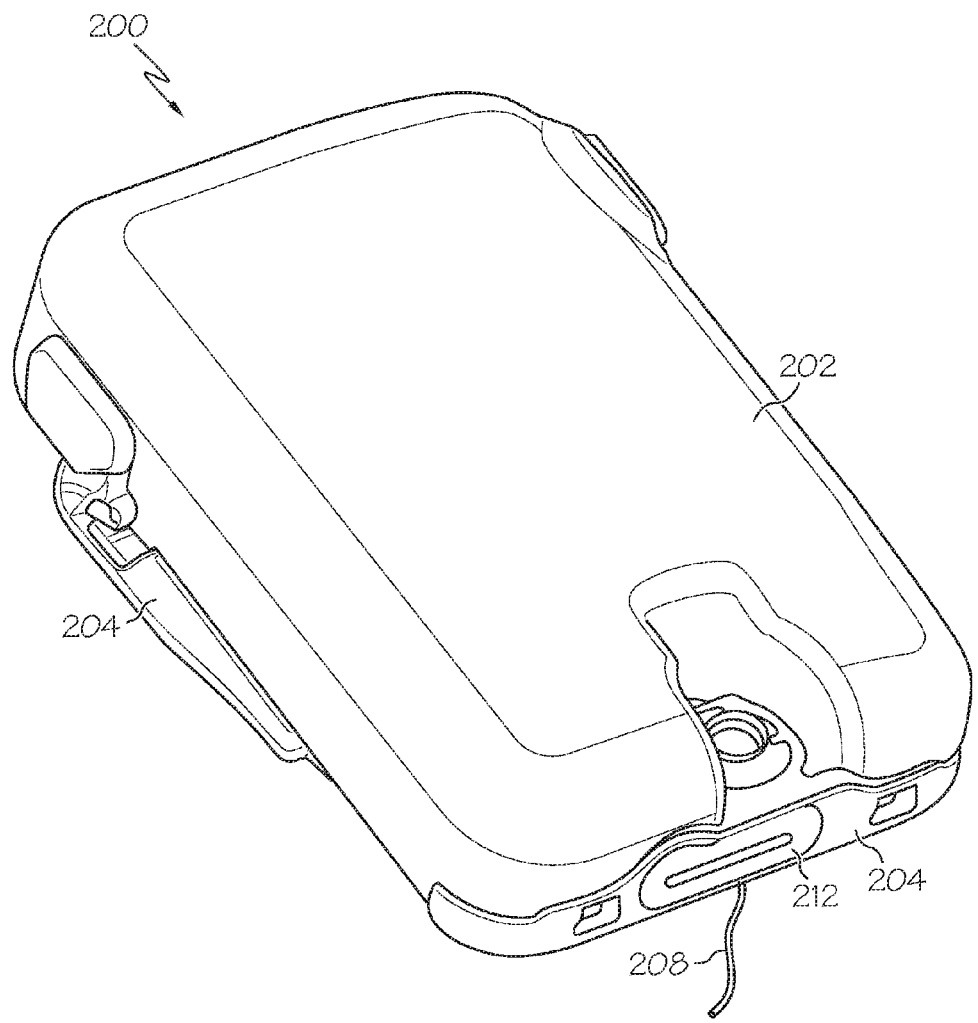
FIG. 2 is a perspective view of an exemplary embodiment of a fluid infusion device suitable for use in the infusion system of FIG. 1.
Figure 3:
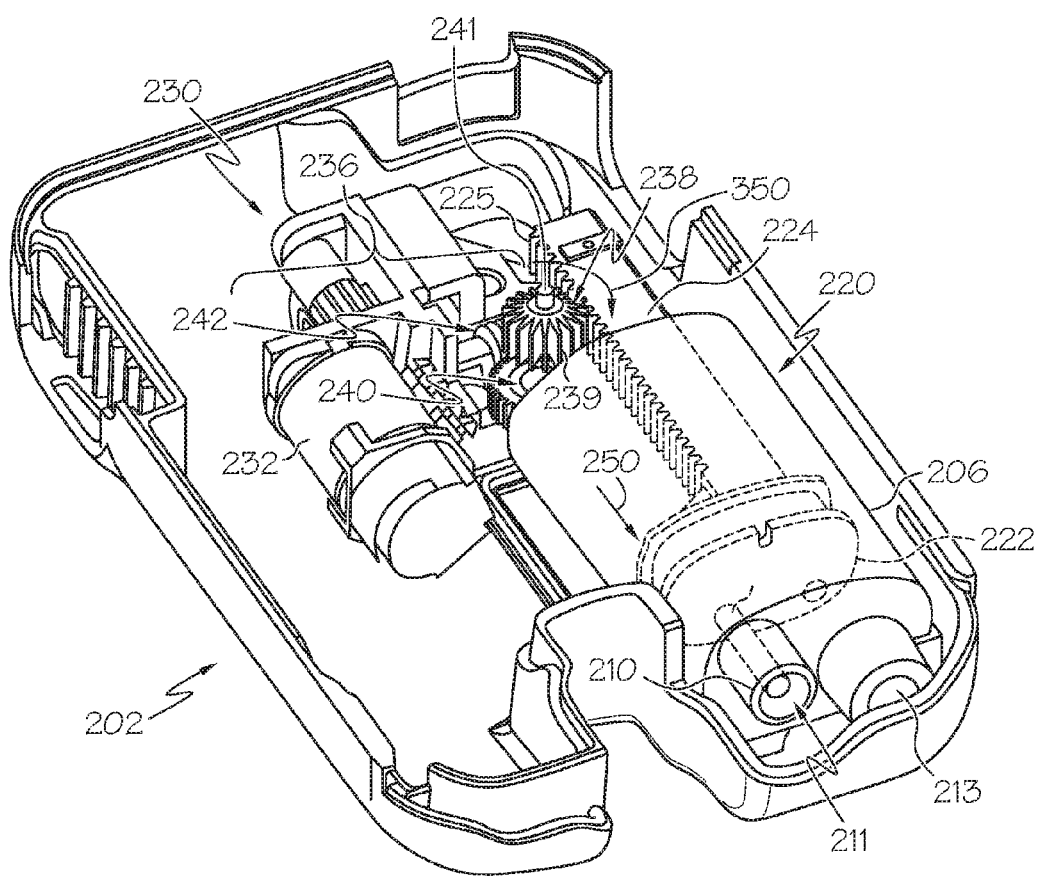
FIG. 3 is a perspective view that depicts internal structure of the durable housing of the fluid infusion device shown in FIG. 2.

FIGS. 2-7 depict an exemplary embodiment of a fluid infusion device 200 suitable for use as the infusion device 102 in the infusion system 100 of FIG. 1. FIGS. 2-3 depict perspective views of the fluid infusion device 200, which includes a durable housing 202 and a base plate 204. While FIG. 2 depicts the durable housing 202 and the base plate 204 as being coupled together, in practice, the durable housing 202 and/or the base plate 204 may include features, structures, or elements to facilitate removable coupling (e.g., pawls, latches, rails, slots, keyways, buttons, or the like) and accommodate a removable/replaceable fluid reservoir 206. As illustrated in FIG. 3, in exemplary embodiments, the fluid reservoir 206 mates with, and is received by, the durable housing 202. In alternate embodiments, the fluid reservoir 206 mates with, and is received by, the base plate 204.

In exemplary embodiments, the base plate 204 is temporarily adhered to the skin of the user, as illustrated in FIG. 1 using, for example, an adhesive layer of material. After the base plate 204 is affixed to the skin of the user, a suitably configured insertion device or apparatus may be used to insert a fluid delivery needle or cannula 208 into the body of the user. The cannula 208 functions as one part of the fluid delivery path associated with the fluid infusion device 200. Although not illustrated in FIG. 2, in some embodiments, the cannula 208 may be part of an infusion set that includes a length of tubing coupled between the reservoir 206 and the cannula 208 to provide a fluid delivery path between the reservoir 206 and the cannula 208 via the tubing. The durable housing 202 receives the fluid reservoir 206 and retains the fluid reservoir 206 in a substantially fixed position and orientation with respect to the durable housing 202 and the base place 204 while the durable housing 202 and the base plate 204 are coupled. The durable housing 202 is configured to secure to the base plate 204 in a specified orientation to engage the fluid reservoir 206 with a reservoir port receptacle formed in the durable housing 202. In particular embodiments, the fluid infusion device 200 includes certain features to orient, align, and position the durable housing 202 relative to the base plate 204 such that when the two components are coupled together, the fluid reservoir 206 is urged into the reservoir port receptacle to engage a sealing assembly and establish a fluid seal.

In exemplary embodiments, the fluid reservoir 206 includes a fluid delivery port 210 that cooperates with the reservoir port receptacle to establish a fluid delivery path. In this regard, the fluid delivery port 210 has an interior 211 defined therein that is shaped, sized, and otherwise configured to receive a sealing element when the fluid reservoir 206 is engaged with the reservoir port receptacle on base plate 204. The sealing element forms part of a sealing assembly for the fluid infusion device 200 and preferably includes one or more sealing elements and/or fluid delivery needles configured to establish fluid communication from the interior of the reservoir 206 to the cannula 208 via the fluid delivery port 210 and a mounting cap 212, and thereby establish a fluid delivery path from the reservoir 206 to the user via the cannula 208. In the illustrated embodiment, the fluid reservoir 206 includes a second fluid port for receiving fluid. For example, the second fluid port 213 may include a pierceable septum, a vented opening, or the like to accommodate filling (or refilling) of the fluid reservoir 206 by the patient, a doctor, a caregiver, or the like.

As illustrated in FIG. 3, the reservoir 206 includes a barrel 220 for containing fluid and a plunger 222 (or stopper) positioned to push fluid from inside the barrel 220 of the reservoir 206 along the fluid path through the cannula 208 to the user. A shaft 224 is mechanically coupled to or otherwise engages the plunger 222, and the shaft 224 has exposed teeth 225 that are configured to mechanically couple or otherwise engage the shaft 224 with a gear 238 of a drive system 230 contained in the durable housing 202. In this regard, the shaft 224 functions as a rack gear as part of a rack and pinion gear configuration. Although the subject matter may be described herein in the context of the shaft 224 being integral with or otherwise part of the plunger 222, in practice, the shaft 224 and the plunger 222 may be provided separately.

Figure 4:
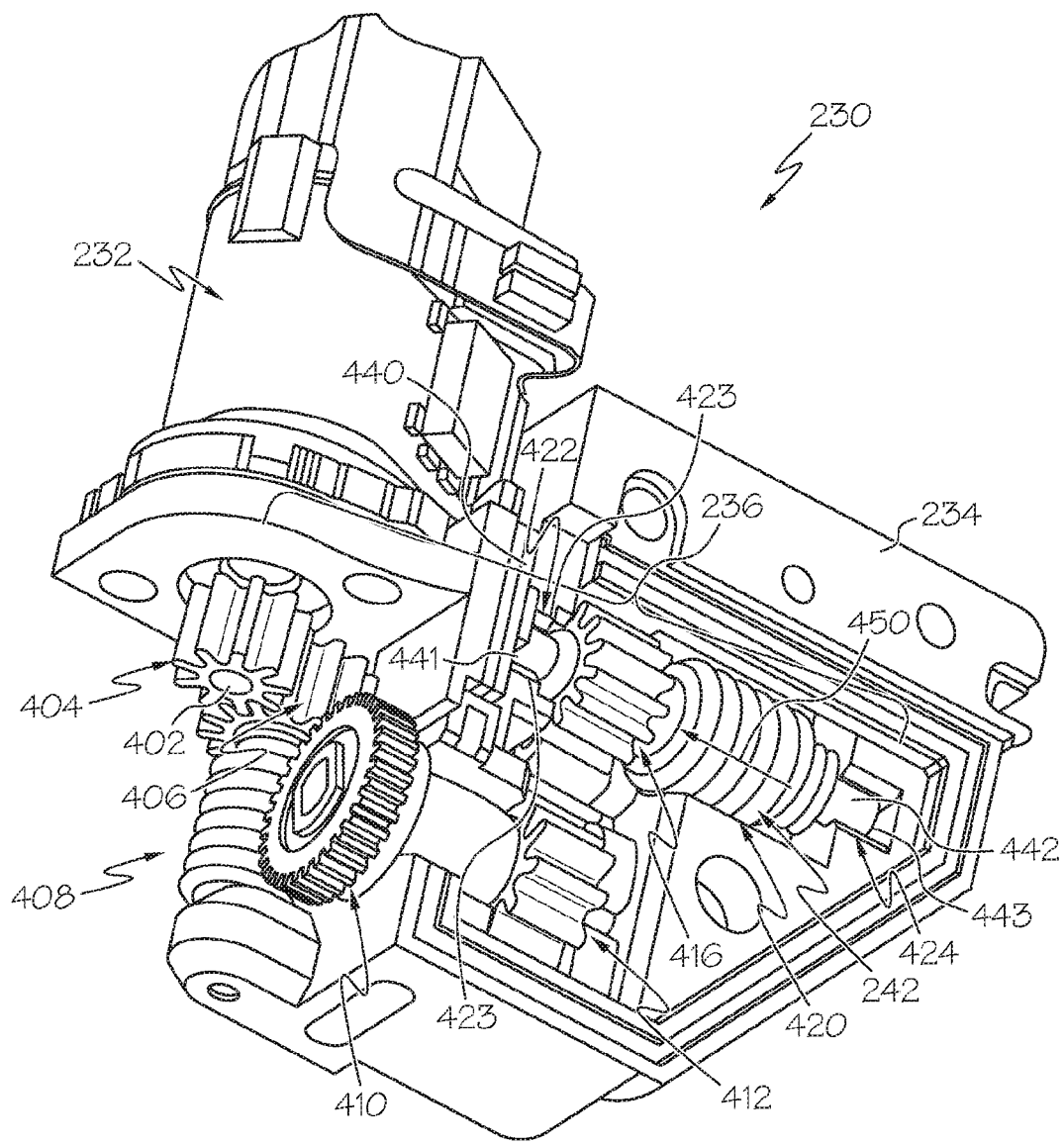
FIG. 4 is a perspective view of the drive system in the durable housing of the fluid infusion device of FIGS. 2-3.
Figure 5:
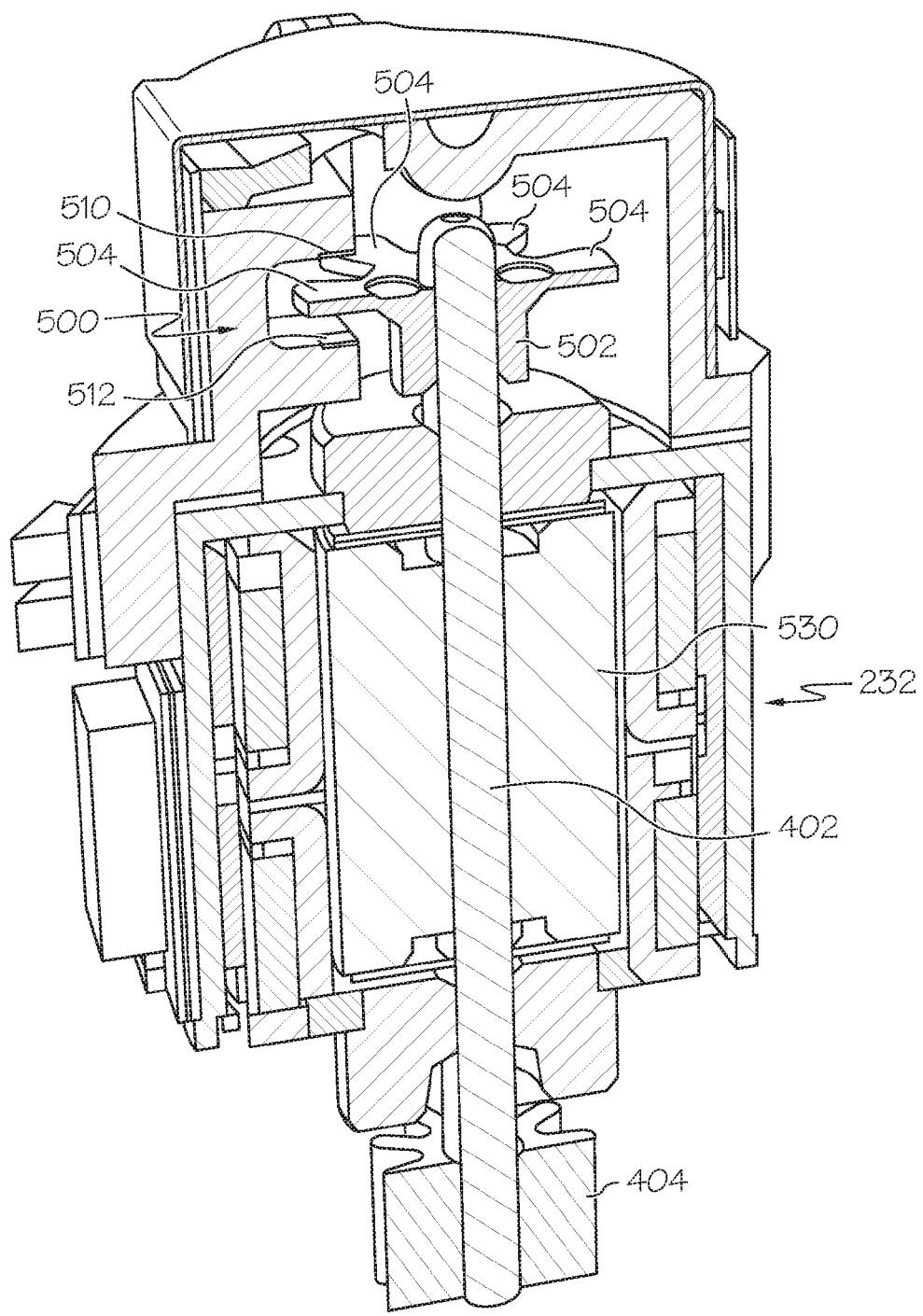
FIG. 5 is cross-sectional perspective view of the motor of drive system of FIG. 4 illustrating a sensor integrated therein.
Figure 6:
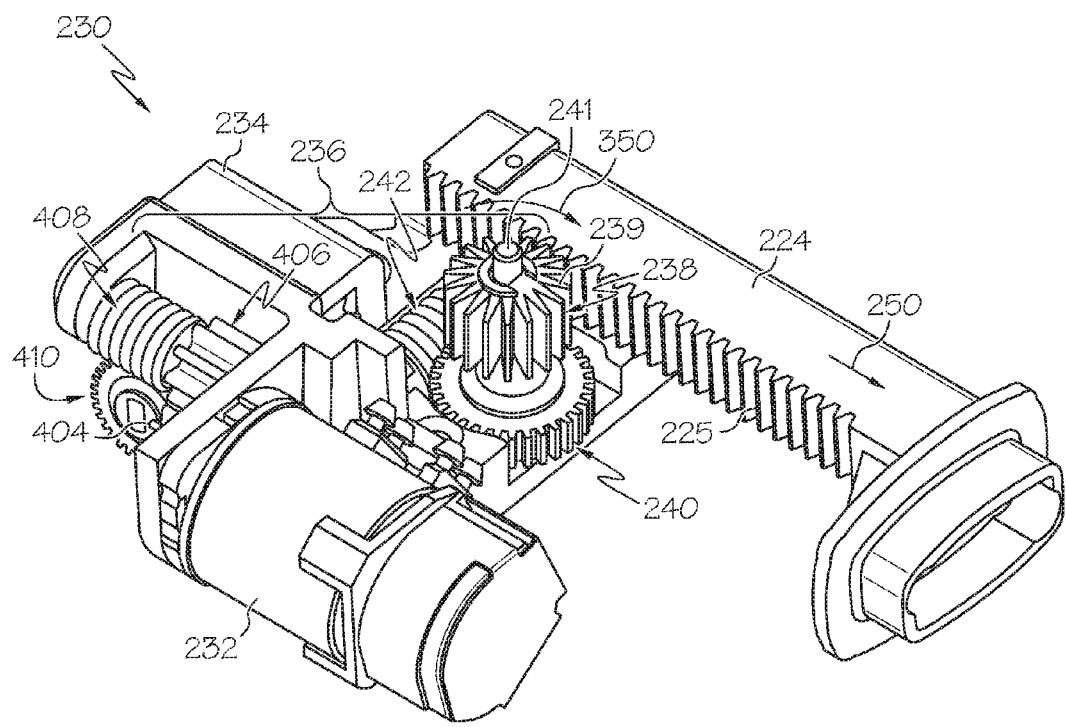
FIG. 6 is a perspective view illustrating the drive system engaged with the shaft of the plunger when the fluid reservoir is seated within the durable housing of FIG. 3.

FIGS. 4-6 depict perspective and cross-sectional views of the drive system 230 provided in the durable housing 202. Various aspects of the motor drive system 230 may be similar to those described in U.S. patent application Ser. No. 13/049,803. The drive system 230 includes a motor 232 having a rotor 530 that is mechanically coupled to a gear assembly 236 that translates rotation of the rotor 530 to translational displacement the plunger 222 in the direction 250 of the fluid delivery port 210 to deliver fluid from the reservoir 206 to a user. Accordingly, the direction 250 may alternatively be referred to herein as the fluid delivery direction 250.

In exemplary embodiments, the motor 232 is realized as a DC motor, such as a stepper motor or brushless DC motor capable of precisely controlling the amount of displacement of the plunger 222 during operation of the infusion device 200. As best illustrated in FIGS. 4-5, in exemplary embodiments, the rotor 530 of the motor 232 is mechanically coupled to a rotary shaft 402, which, in turn, is mechanically coupled to a first gear 404 of the gear assembly 236. In the illustrated embodiment of FIGS. 4-5, the first gear 404 is coaxial and/or concentric to and disposed about the rotary shaft 402, and the first gear 404 is affixed to or otherwise integrated with the rotary shaft 402 such that the first gear 404 and the rotary shaft 402 rotate in unison. The gear assembly 236 also includes a pinion gear 238 having exposed teeth 239 that are configured to mate with or otherwise engage the exposed teeth 225 on the shaft 224 when the reservoir 206 is seated in the durable housing 202, such that rotation or displacement of the pinion gear 238 in rotational delivery direction 350 produces a corresponding translational displacement of the shaft 224 and/or plunger 222 in the fluid delivery direction 250 to deliver fluid to the user.

During operation of the fluid infusion device 200, when the motor 232 is operated to rotate the rotor 530, the rotary shaft 402 rotates in unison with the rotor 530 to cause a corresponding rotation of the first gear 404, which, in turn, actuates the gears of the gear assembly 236 to produce a corresponding rotation or displacement of the pinion gear 238, which, in turn, displaces the shaft 224. In this manner, the rotary shaft 402 translates rotation (or displacement) of the rotor 530 into a corresponding rotation (or displacement) of the gear assembly 236 such that the teeth 239 of the pinion gear 238 apply force to the teeth 225 of the shaft 224 of the plunger 222 in the fluid delivery direction 250 to thereby displace the plunger 222 in the fluid delivery direction 250 and dispense, expel, or otherwise deliver fluid from the barrel 220 of the reservoir 206 to the user via the fluid delivery path provided by the cannula 208.

Referring to FIG. 5, in an exemplary embodiment, a sensor 500 is configured to measure, sense, or otherwise detect rotation (or displacement) of the rotary shaft 402 and/or the rotor 530 of the motor 232. For convenience, but without limitation, the sensor 500 may alternatively be referred to herein as a motor position sensor or rotor position sensor. The sensor 500 may be utilized to provide closed-loop control of the motor 232, such as, for example, as described in U.S. patent application Ser. No. 13/425,174, the subject matter of which is hereby incorporated by reference in its entirety. In exemplary embodiments, the rotary shaft 402 includes a detectable feature that is measurable or otherwise detectable by the motor position sensor 500. In the illustrated embodiment, a rotary member (or wheel) 502 is provided on the rotary shaft 402 and includes a plurality of protruding features (or arms) 504 that are measurable or otherwise detectable by the motor position sensor 500. In the illustrated embodiment, the wheel 502 is coaxial and/or concentric to and disposed about the rotary shaft 402, and the wheel 502 is affixed to or otherwise integrated with the rotary shaft 402 such that the wheel 502 and the rotary shaft 402 rotate in unison. In this manner, rotation (or displacement) of the wheel 502 corresponds to the displacement of the rotary shaft 402 and/or the rotor 530 of the motor 232.

In exemplary embodiments, the sensor 500 is realized as an incremental position sensor configured to measure, sense, or otherwise detect incremental rotations of the rotary shaft 402 and/or the rotor 530 of the motor 232. For example, in accordance with one or more embodiments, the sensor 500 is realized as a rotary encoder. In alternative embodiments, the sensor 500 may be realized using any other suitable sensor, such as (but not limited to) a magnetic sensor, optical sensor (or other light detector), tactile sensor, capacitive sensor, inductive sensor, and/or the like. In exemplary embodiments, the incremental position sensor 500 may be configured to count or otherwise sense incremental rotations of the motor 232 via the wheel 502, for example, by counting each time a protruding feature 504 passes by the sensor 500. In this regard, when the number of protruding features 504 equals or otherwise corresponds to the number of discrete motor steps of the stepper motor 232, the incremental position sensor 500 counts or otherwise senses the number of motor steps traversed by the rotary shaft 402 and/or rotor of the motor 232. In some embodiments, the sensor 500 includes an emitter 510 and a detector 512 disposed on opposite sides of the wheel 502 such that at least a portion of the protruding features 504 passes between the emitter 510 and the detector 512 as the wheel 502 rotates. In this regard, the sensor 500 may detect or otherwise count each instance when a protruding feature 504 interrupts a transmission from the emitter 510 to the detector 512. Alternatively, the sensor 500 may detect or otherwise count each instance a transmission from the emitter 510 to the detector 512 is uninterrupted or otherwise completed (e.g., via gaps between protruding features 504).

Referring now to FIGS. 3-7, in exemplary embodiments, the gear assembly 236 includes a spur gear 240 that is mechanically coupled to the pinion gear 238 via a common axle 241 so that the spur gear 240 and the pinion gear 238 rotate in unison. The gear assembly 236 also includes a worm gear 242 that engages with the teeth of the spur gear 240 to translate rotation of the worm gear 242 into a corresponding rotation of the axle 241 of the pinion gear 238. The worm gear 242 and the spur gear 240 cooperatively provide a worm drive arrangement that prevents the pinion gear 238 from being backdriven by external forces applied (e.g., by the shaft 224 or reservoir 206) to the pinion gear 238 in the direction opposite the fluid delivery direction 250. To put it another way, the motor 232 may be operated to rotate the worm gear 242, and thereby rotate the pinion gear 238 in the positive delivery rotational direction 350, but rotation of the worm gear 242 is not capable of being achieved merely by rotating the pinion gear 238 in the negative delivery direction. Rather, force applied to the pinion gear 238 in the direction opposite the rotational delivery direction 350 results in axial forces applied to the worm gear 242 by the spur gear 240, which, in turn, may result in axial displacement of the worm gear 242.

As best illustrated in FIG. 4, the gear assembly 236 includes a plurality of gears 404, 406, 408, 410, 412, 414, 416 configured to translate rotation of the rotary shaft 402 into a corresponding rotation of the worm gear 242, and thereby, a corresponding rotation of the pinion gear 238. As illustrated, the gear assembly 236 includes a spur gear 406 having teeth that engage with the gear 404 coupled to the rotary shaft 402, so that rotation of the gear 404 results in a corresponding amount of rotation of the spur gear 406. The spur gear 406 shares a common axle with a worm gear 408 so that the spur gear 406 and the worm gear 408 rotate in unison, with the worm gear 408 engaging another spur gear 410 to provide another worm drive arrangement. Spur gear 410 shares a common axle with another spur gear 412 so that the gears 410, 412 rotate in unison. Spur gear 412 engages another spur gear 414 (illustrated in FIG. 7), which, in turn, engages a spur gear 416 sharing a common axle 442 with the worm gear 242, so that the spur gear 416 and the worm gear 242 rotate in unison. By virtue of this configuration, the worm gear 408 translates rotation of the spur gear 404 into a corresponding rotation of the spur gear 412, which engages the spur gear 414 to rotate the spur gear 416 and the axle 442, and thereby rotate the worm gear 242. Thus, the rotary shaft 402 is coupled to the worm gear 242, and thereby, the pinion gear 238, so that rotation of the rotary shaft 402 produces a corresponding rotation of the worm gear 242, which, in turn, produces a corresponding rotation of the pinion gear 238.

Still referring to FIGS. 3-7, in exemplary embodiments, the durable housing 202 includes or otherwise incorporates a frame structure 234 that provides support to various gears of the gear assembly 236. In this regard, the frame structure 234 is realized as a substantially rigid material that the axles of the gears may be mounted to, restrained by, or otherwise supported by to ensure that the gear assembly 236 translates rotation of the rotary shaft 402 into rotation of the pinion gear 238 without gears of the gear assembly 236 becoming disengaged. Additionally, the frame structure 234 may be utilized to mount the motor 232 to the gear assembly 236 so that the rotary shaft 402 is maintained in engagement with the spur gear 404.

Figure 7:
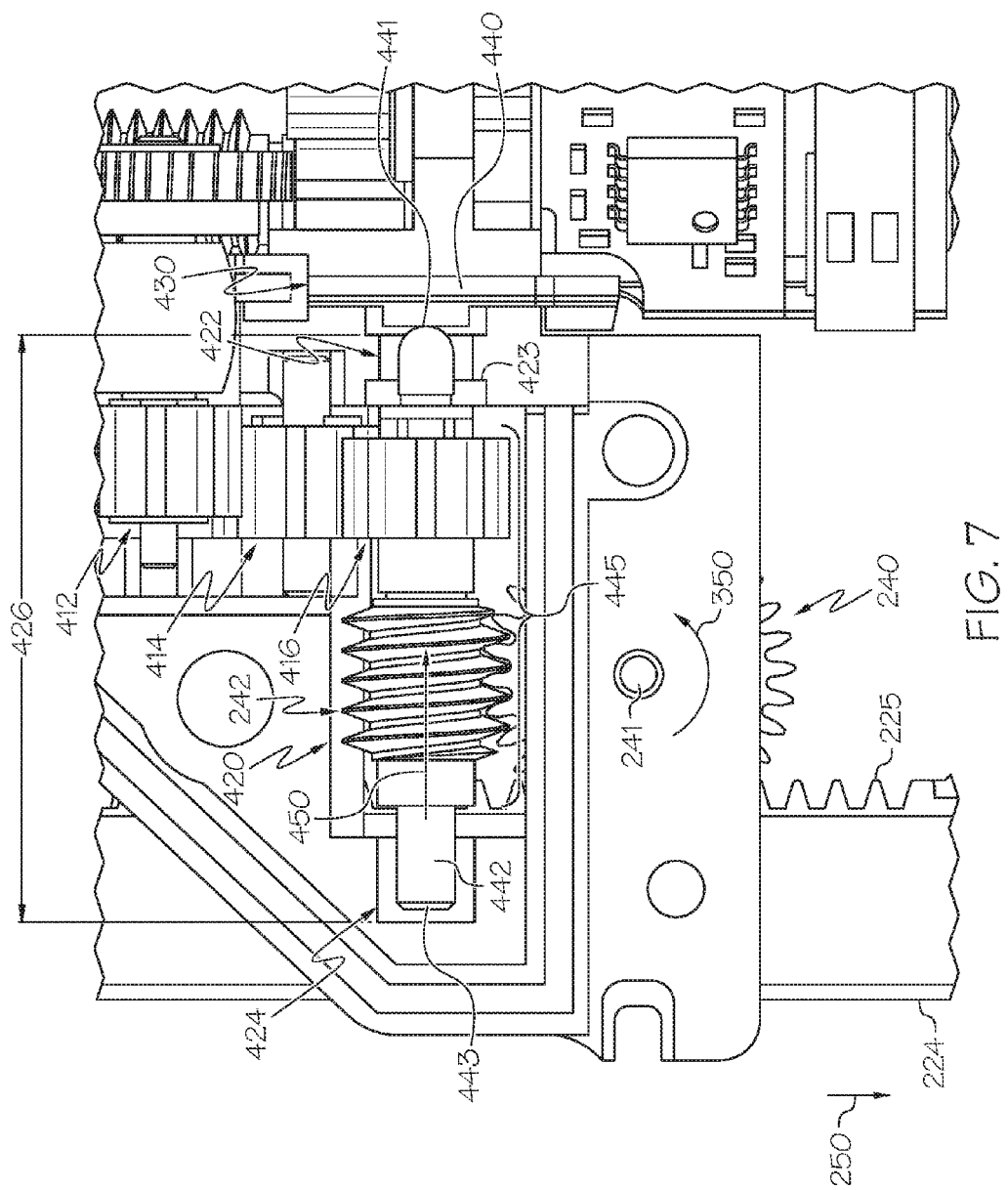
FIG. 7 is a plan view illustrating the gear assembly of the drive system engaged with the shaft of the plunger when the fluid reservoir is seated within the durable housing of FIG. 3.

As best illustrated by FIG. 4 or FIG. 7, the frame structure 234 includes a voided region 420 that substantially circumscribes the axle 442 of the worm gear 242 about its longitudinal axis to maintain the axle 442 and/or the worm gear 242 in a substantially fixed plane with respect to the frame structure 234. In this regard, the illustrated voided region 420 includes an opening 422 at one end having a first end 441 of the axle 442 disposed therein to prevent displacement of that end 441 of the axle 442 perpendicularly to its longitudinal axis, and similarly, the voided region 420 includes a cutout portion 424 of the frame structure 234 that has the opposite end 443 of the axle 442 disposed therein to prevent displacement of that end 443 of the axle 442 perpendicularly to its longitudinal axis. In this manner, the frame structure 234 restricts or otherwise prevents displacement of the axle 442 and/or worm gear 242 perpendicularly to its longitudinal axis. As described in greater detail below, the total length (illustrated by arrow 426) of the voided region 420 is greater than the length of the axle 442 so that the axle 442 (and thereby, the worm gear 242) is capable of axial displacement until either end 441, 443 of the axle 442 is restrained or otherwise prevented from further axial displacement by the frame structure 234. In this regard, the respective circumferences of the opening 422 and the cutout portion 424 are less than the circumference of the central portion 445 of the axle 442 to limit axial displacement of the worm gear 242 so that the spur gear 416 is maintained in engagement with the spur gear 414 as the axle 442 is displaced.

In addition to the voided region 420, the frame structure 234 also includes another cutout region (or slot) 430 aligned with the longitudinal axis of the axle 442 and the opening 422 at the end of the voided region 420. The cutout region 430 includes a force sensing arrangement 440 (or force sensor) that measures or otherwise senses an axial force exerted on or otherwise provided by the axle 442 in an axial direction 450. In this regard, when the motor 232 is operated to rotate the pinion gear 238 in the direction 350 that results in displacement of the shaft 224 in the fluid delivery direction 250, the corresponding rotation of the worm gear 242 results in the axle 442 of the worm gear 242 being displaced in the axial direction 450 towards the force sensor 440 by virtue of the resistance force opposing displacement of the shaft 224 and/or plunger 222 provided by the fluid within the barrel 220 of the reservoir 206. This oppositional force is applied or otherwise transferred via the spur gear 240 so that the end 441 of the axle 442 of the worm gear 242 extends through the opening 422 and contacts the force sensor 440, as illustrated in FIG. 7. In this regard, the axial direction 450 corresponds to the direction of force applied to the worm gear 242 when the shaft 224 and/or plunger 222 is displaced in the fluid delivery direction 250, and accordingly, may alternatively be referred to herein as the axial delivery direction 450.

As external forces resist or otherwise prevent displacement of the shaft 224 and/or plunger 222 in the fluid delivery direction 250 (e.g., due to a fluid path occlusion), rotation of the pinion gear 238 and the spur gear 240 is resisted or otherwise prevented, so that the torque applied by the motor 232 to the worm gear 242 via the gear assembly 236 is translated into an axial force exerted on the force sensor 440 by the axle 442. Because the worm drive arrangement provided by the worm gear 242 and spur gear 240 is incapable of being backdriven, once the axle 442 of the worm gear 242 is displaced in the axial direction 450 and restricted from further displacement in the axial direction 450 by the frame structure 234 and/or force sensor 440, the pinion gear 238 is effectively incapable of being rotated by a non-negligible amount in the direction opposite the rotational direction 350 corresponding to the fluid delivery direction 250, thereby ensuring oppositional forces are transferred to the force sensor 440 via the worm drive arrangement. In some embodiments, the force sensor 440 includes one or more sensing elements, wherein an electrical characteristic of a respective sensing element is influenced by the amount of compressive force exerted on the force sensor 440 by the axle 442. For example, force sensor 440 may include one or more strain gauge elements, piezoresistive elements, or the like that are electrically configured to provide a Wheatstone bridge circuit that provides an output electrical signal indicative of the force applied to the force sensor 440.

It should be understood that FIGS. 2-7 depict merely one exemplary embodiment of an infusion device 200, and the subject matter described herein is not intended to be limited to any particular type of infusion device or delivery configuration. For example, in practice, an infusion device may include any of a number of different types of infusion sets with different lengths of tubing and/or different types of fluid delivery components that establish or otherwise provide a fluid path from the reservoir within the infusion device to a user. Furthermore, practical embodiments of the infusion device may include a different configuration of the drive system 230, motor 232 and/or force sensor 440 with respect to the shaft 224 and/or plunger 222 of the reservoir 206, such as, for example, a coaxially aligned drive system as described in U.S. patent application Ser. No. 12/908,807, the subject matter of which is hereby incorporated by reference in its entirety.

Figure 8:
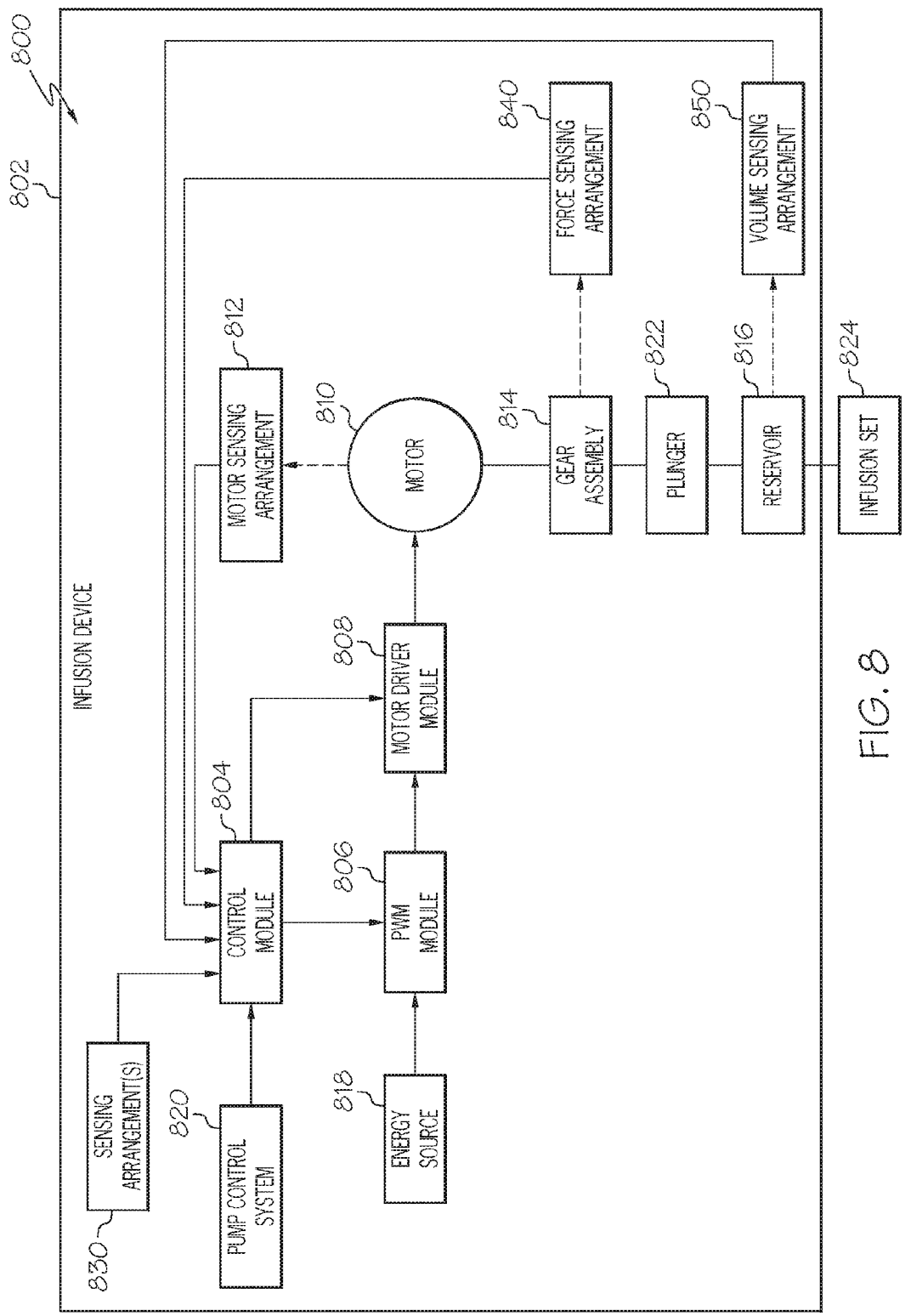
FIG. 8 is a block diagram of a control system that may be implemented or otherwise supported by a fluid infusion device in one or more exemplary embodiments.

FIG. 8 depicts an exemplary embodiment of a control system 800 suitable for use with an infusion device 802 in an infusion system, such as infusion device 200 or infusion device 102 in the infusion system 100. The illustrated control system 800 includes, without limitation, a control module 804, a pulse-width modulation (PWM) module 806, a motor driver module 808, a motor 810 (e.g., motor 232), and a motor (or rotor) position sensing arrangement 812 (e.g., sensor 500). The control system 800 is suitably configured to operate the motor 810 to displace a plunger 822 (e.g., plunger 222) of a reservoir 816 (e.g., reservoir 206) via a gear assembly 814 (e.g., gear assembly 236) and provide a desired amount of fluid to a user in response to a dosage command. The pump control system 820 generally represents the electronics and/or other components of the infusion system configured to process sensor (or measurement) data (e.g., from sensing arrangement 104) pertaining to a condition of the user and control operation of the fluid infusion device 802. The pump control system 820 generates the dosage command indicative of a desired amount of fluid to be delivered according to a desired infusion delivery program in a manner that is influenced by sensor data measured by and/or received from the sensing arrangement 104 or otherwise dictated by the user.

It should be understood that FIG. 8 is a simplified representation of the control system 800 for purposes of explanation and is not intended to limit the subject matter described herein in any way. For example, in practice, the features and/or functionality of the control module 804 may be implemented by or otherwise integrated into the pump control system 820, or vice versa. In some embodiments, the features and/or functionality of the pump control system 820 may be implemented by control electronics located in the fluid infusion device 102, 200, the CCD 106 and/or the computer 108. Additionally, while the illustrated control system 800 may be described in the context of utilizing pulse-width modulated voltage to operate a brushless DC or stepper motor, the subject matter described herein is not limited to any particular type of motor 810 or any particular technique for driving or otherwise controlling the motor 810. For example, in alternative embodiments, the motor driver module 808 may apply a DC voltage from an energy source 818 directly to one or more sets of stator windings of the motor 810 (e.g., without pulse-width modulation) or the motor driver module 808 may convert the DC voltage from the energy source 818 to an alternating current (AC) voltage and/or current as appropriate to the type of motor 810 being utilized.

In exemplary embodiments, the control system 800 includes a force sensing arrangement 840 (e.g., force sensing arrangement 440) that provides an output indicative of the reactionary force exerted by the plunger 822 in opposition to displacement of the plunger 822. In this regard, the force that is sensed, detected, measured, or otherwise quantified by the force sensing arrangement 840 is influenced by operation of the motor 810 to displace the plunger 822. In one or more exemplary embodiments, the control module 804 is coupled to the force sensing arrangement 840 to obtain, receive, sample, or otherwise monitor the output of the force sensing arrangement 840, apply a matched filter to the output of the force sensing arrangement 840, and detect a condition of interest associated with that matched filter based on a magnitude of the filtered output. For example, the control module 804 may detect an occlusion condition in a fluid path from the infusion device 802 to a user by applying a matched filter associated with an occlusion condition to the output of the force sensing arrangement 840 and detecting or otherwise identifying when the filtered output is greater than an occlusion force threshold value. As described above in the context of FIGS. 3-7, in accordance with one or more embodiments, the force sensing arrangement 840 may be integrated with the gear assembly 814, such that the reactionary force of the plunger 822 is transferred to the force sensing arrangement 840 via the gear assembly 814.

As illustrated, in accordance with one or more embodiments, the control system 800 may also include one or more additional sensing arrangements 830, 850 that provide an output indicative of a respective characteristic that is influenced by operation of the motor 810 and/or infusion device 802. For example, the control system 800 may include a volume sensing arrangement 850 that senses, detects, measures, or otherwise quantifies the volume (or amount) of fluid remaining in the fluid reservoir 816. In one embodiment, another sensing arrangement 830 may be realized as a sensing arrangement (e.g., sensing arrangement 104) that is configured to sense, detect, measure, or otherwise quantify a characteristic indicative of a biological condition of a user (e.g., a blood glucose level) of the infusion device 802. In another embodiment, the additional sensing arrangement 830 may be a flow rate sensing arrangement that quantifies a rate of delivery from the reservoir 816 to the user. In a similar manner as described in the context of the force sensing arrangement 840, the control module 804 may be coupled to a respective sensing arrangement 830, 850 to obtain, receive, sample, or otherwise monitor the output of the respective sensing arrangement 830, 850, apply a matched filter to the output of the respective sensing arrangement 830, 850, and detect a condition of interest (e.g., an occlusion condition or some other condition) corresponding to that matched filter based on a magnitude of the filtered output. For example, the control module 804 may detect a leakage condition in the reservoir 816 or elsewhere in a fluid path from the infusion device 802 to a user via an infusion set 824 by applying a matched filter associated with a leakage condition to the output of the volume sensing arrangement 850 and detecting or otherwise identifying when the filtered output is greater than (or less than) to a leakage threshold value. Accordingly, while the subject matter may be described herein primarily in the context of detecting an occlusion condition based on the filtered output from the force sensing arrangement 840 for purposes of explanation, the subject matter is not necessarily limited to a particular condition being detected or a particular sensing arrangement 830, 840, 850, 850 being utilized to detect that condition.

In an exemplary embodiment, the motor 810 is a stepper motor or brushless DC motor having a toothed rotor and a number of sets of windings, wherein the number of teeth on the rotor along with the number of winding sets and the physical arrangement of the winding sets with respect to the rotor teeth provides a finite number of motor steps within a revolution of the rotor. In this regard, as used herein, a "motor step" or any variant thereof should be understood as referring to an incremental rotation of the rotor of the motor 810 that is dictated by the number of teeth of the rotor along with the number and/or arrangement of the winding sets. In the exemplary infusion pump embodiment described above in the context of FIGS. 2-7, the rotor of the motor 232, 810 is mechanically coupled to the plunger 222, 822 of a reservoir 206, 816 via a gear assembly 236, 814 and a shaft 224, wherein the gear assembly 236, 814 translates rotation of the rotor of the motor 810 into a corresponding amount of displacement of the shaft, which in turn, displaces the plunger 222, 822 into the barrel 220 of the reservoir 206, 816 to deliver fluid (e.g., insulin) to the body of a user via an infusion set 824. The infusion set 824 may include a cannula (e.g., cannula 208), a length of tubing, and/or other components capable of establishing a sealed fluid delivery path from the reservoir 206, 816, 816 to the body of the user.

Still referring to FIG. 8, in the illustrated embodiment, the PWM module 806 generally represents the combination of circuitry, hardware and/or other electrical components configured to generate a pulse-width modulated voltage output applied to the motor 810 via the motor driver module 808. In an exemplary embodiment, the PWM module 806 is coupled to an energy source 818, such as a battery housed within the infusion device 802 (e.g., in the durable housing 202), to receive a supply voltage. Based on a duty cycle setting for the PWM module 806, the PWM module 806 generates or otherwise produces a pulse-width modulated voltage output that oscillates between the supply voltage provided by the energy source 818 and a ground (or reference) voltage over a time interval (e.g., the PWM period), wherein the pulse-width modulated voltage output is equal to the supply voltage for a percentage of the time interval corresponding to the duty cycle setting. For example, if the supply voltage provided by the energy source 930 is equal to five volts and the duty cycle setting is equal to 30%, then the pulse-width modulated voltage output generated by the PWM module 806 may be a square wave having a magnitude equal to five volts for 30% of the time interval and zero volts for the remaining 70% of the time interval. In this regard, the duty cycle setting corresponds to the width of a portion of the square wave (e.g., the portion corresponding the supply voltage), and accordingly, the duty cycle setting may alternatively be referred to herein as the PWM width setting. In one or more embodiments, the control module 804 is coupled to the PWM module 806 to adjust, modify, or otherwise control the duty cycle setting of the PWM module 806.

The motor driver module 808 generally represents the combination of circuitry, hardware and/or other electrical components configured to sequentially apply a voltage provided at a supply voltage input of the motor driver module 808 to one or more sets of stator windings of the motor 810 in a particular order that produces a corresponding number of commanded motor steps of rotation by the rotor of the motor 810. The supply voltage input of the motor driver module 808 is coupled to the output of the PWM module 806, such that the motor driver module 808 provides the pulse-width modulated voltage output from the PWM module 806 to the one or more sets of stator windings of the motor 810 in a particular order under control of the control module 804. In this regard, in some embodiments, the motor driver module 808 is coupled to the control module 804 to receive a commanded number of motor steps from the control module 804, wherein in response to the commanded number of motor steps, the motor driver module 808 sequentially applies the pulse-width modulated voltage from the PWM module 806 to the sets of stator windings of the motor 810 in the appropriate order to produce the commanded number of motor steps. In other embodiments, the control module 804 may operate the motor driver module 808 to produce the commanded number of motor steps. In accordance with one or more embodiments, the frequency at which the motor driver module 808 is operated (e.g., the frequency at which the pulse-width modulated voltage is changed from being applied to one stator winding set to another stator winding set) is less than the frequency of the pulse-width modulated voltage output from the PWM module 806, such that the pulse-width modulated voltage output oscillates between the supply voltage and the ground voltage multiple times over the time period (e.g., the inverse of the motor driver frequency) during which the pulse-width modulated voltage output is applied to a particular set of stator windings of the motor 810.

In an exemplary embodiment, the motor position sensing arrangement 812 is realized as an incremental position sensor, such as a rotary encoder, that is configured to sense, measure, or otherwise detect an incremental rotation of the rotor of the motor 810 in a similar manner as described above in the context of the sensor 500 of FIG. 5. In exemplary embodiments, the resolution of the position sensor 812 is greater than or equal to the resolution of the motor 810, that is, the number of discrete incremental rotations measurable by the position sensor 812 over one revolution of the rotor of the motor 810 (e.g., the number of detectable features 504) is greater than or equal to the number of discrete motor steps over one revolution of the rotor of the motor 810. The output of the position sensor 812 is coupled to the control module 804 to provide closed-loop control of the motor 810 position. In accordance with one or more embodiments, the output of the position sensor 812 is coupled to the control module 804 to provide dynamic closed-loop PWM control of the motor 810 by adjusting the duty cycle setting of the PWM module 806, for example, as described in U.S. patent application Ser. No. 13/425,174, which is assigned to the assignee of the present application and incorporated by reference herein.

The control module 804 generally represents the hardware, firmware, software, and/or combination thereof that is configured to receive or otherwise obtain a dosage command from the pump control system 820, convert the commanded dosage to a commanded number of motor steps, and command, signal, or otherwise operate the motor driver module 808 to cause the motor 810 to produce the commanded number of motor steps. Depending on the embodiment, the control module 804 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the control module 804, or in any practical combination thereof. In exemplary embodiments, the control module 804 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the control module 804. The computer-executable programming instructions, when read and executed by the control module 804, cause the control module 804 to perform the tasks, operations, functions, and processes described in greater detail below.

Additionally, as described in greater detail below, in accordance with one or more embodiments, the control module 804 stores or otherwise maintains values for filter coefficients for one or more matched filters to be applied to the output of a respective sensing arrangement 830, 840, 850 to detect or otherwise identify the presence of a particular condition of interest associated with the respective matched filter based on the filtered output of the respective sensing arrangement 830, 840, 850. The filter coefficient values of a respective matched filter provide a filter impulse response that corresponds to or otherwise matches an expected (or anticipated) output of the respective sensing arrangement 830, 840, 850 to which it is applied when a condition of interest exists or is otherwise exhibited by the infusion device 802 and/or the fluid delivery path to the user. In this regard, each matched filter is associated with a particular condition of interest to be detected along with the particular sensing arrangement 830, 840, 850 to which the matched filter is to be applied. For example, the control module 804 may maintain a first set filter coefficient values for a first matched filter to be applied to the output of the force sensing arrangement 840 to detect an occlusion condition based on the force measured by the force sensing arrangement 840, and a second set filter coefficient values for a second matched filter to be applied to the output of the volume sensing arrangement 850 to detect an occlusion condition based on the remaining amount of fluid in the reservoir that is measured by the volume sensing arrangement 850.

Additionally, in exemplary embodiments, the matched filters are associated with a particular delivery configuration for the infusion device 802, such as a particular type of infusion set 824 being used with the infusion device 802, a particular type and/or size of reservoir inserted in the infusion device 802, a particular delivery mode (or delivery rate) being implemented by the infusion device 802. The particular type of infusion set 824 may identify a length and/or diameter of tubing used in the infusion set 824, a type of cannula utilized in the infusion set 824, and/or other information describing delivery characteristics of the infusion set 824. For example, a first matched filter for detecting an occlusion condition based on the output of the force sensing arrangement 840 may be associated with a first infusion set having a first tubing length (e.g., between fluid delivery port 210 and cannula 208) and a first type and/or size of reservoir for a basal delivery mode (or rate), while a second matched filter for detecting an occlusion condition based on the output of the force sensing arrangement 840 may be associated with the first infusion set and the first type and/or size of reservoir for a bolus delivery mode (or rate), a third matched filter for detecting an occlusion condition based on the output of the force sensing arrangement 840 may be associated with the first infusion set and a second type and/or size of reservoir for the basal delivery mode (or rate), and a fourth matched filter for detecting an occlusion condition based on the output of the force sensing arrangement 840 may be associated with a second infusion set having a second tubing length and the first type and/or of reservoir for the basal delivery mode (or rate). In this regard, as the delivery mode and/or delivery configuration for the infusion device 802 changes over time, the control module 804 may dynamically select and apply the matched filter associated with the current delivery mode and/or delivery configuration for the infusion device 802.

Figure 9:
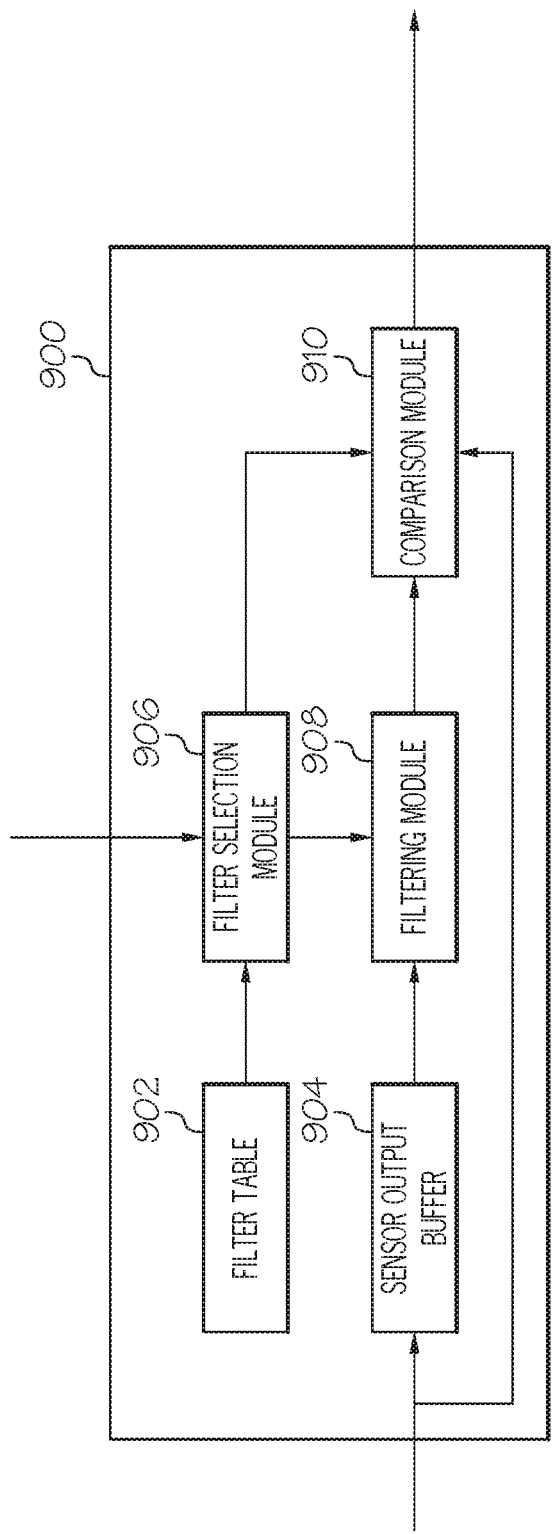
FIG. 9 is a block diagram of a detection module suitable for use in the control system of FIG. 8 in one or more exemplary embodiments.

FIG. 9 depicts an exemplary embodiment of a detection module 900 that may be implemented by the control module 804 to apply a matched filter to the output of a sensing arrangement 830, 840, 850 and detect a condition of interest based on the filtered output. The detection module 900 includes, without limitation, a first data storage element 902 configured to store or otherwise maintain filter configuration information, a second data storage element 904 configured to store or otherwise maintain the recently obtained output of a respective sensing arrangement 830, 840, 850, a filter selection module 906 to select the appropriate filter from the data storage element 902 based on the current delivery configuration for the infusion device 802, a filtering module 908 to apply the selected filter to the recently obtained output values maintained by data storage element 904, and a comparison module 910 to compare the filtered output to one or more threshold values to detect or otherwise identify the condition of interest.

The data storage element 902 may be realized using any suitable memory or other non-transitory computer-readable medium capable of storing or otherwise maintaining filter configuration information. For purposes of explanation, the data storage element 902 is alternatively referred to herein as the filter table. The filter configuration information stored by the filter table 902 includes the filter coefficient values for a respective filter along with information identifying the condition of interest associated with that filter, the sensing arrangement associated with that filter, one or more threshold values that the filtered output from that sensing arrangement should be compared to identify that condition of interest, and the delivery mode and/or delivery configuration for the infusion device 200, 802 that filter is capable of being used with.

The data storage element 904 is coupled to the output of a respective sensing arrangement 830, 840, 850 and may be realized be realized using any suitable memory or other non-transitory computer-readable medium capable of storing or otherwise maintaining recently obtained values for the output of that respective sensing arrangement 830, 840, 850. In this regard, the data storage element 904 stores values corresponding to the characteristic that was sensed, measured, or otherwise detected and quantified by the respective sensing arrangement 830, 840, 850. For purposes of explanation, the data storage element 904 is alternatively referred to herein as the sensor output buffer. In exemplary embodiments, the sensor output buffer 904 stores a number of values corresponding to the output of the respective sensing arrangement 830, 840, 850 that were sampled, quantified, or otherwise obtained at a preceding sampling time. For example, the sensor output buffer 904 may store the fifty most recently sampled output values for a respective sensing arrangement 830, 840, 850. In one embodiment, the number of sensor output values stored by the sensor output buffer 904 is greater than or equal to the length of the longest filter maintained by the filter table 902, that is, the number of sensor output values stored by the sensor output buffer 904 may be greater than or equal to the number of filter coefficient values for the filter in the filter table 902 having the most filter coefficient values associated therewith.

The filter selection module 906 generally represents the component of the detection module 900 that is coupled to the pump control system 820 or some other components of the infusion device 802 to receive or otherwise obtain information identifying the current delivery mode and/or current delivery configuration of the infusion device 802, such as, for example, the type of infusion set 824 currently being used with the infusion device 802, the type and/or size of the reservoir 206, 816 currently inserted in the infusion device 802, the current delivery mode being implemented by the infusion device 802 and/or control module 804, and the like. The filter selection module 906 is coupled to the filter table 902, and based on the current delivery mode and/or current delivery configuration, the filter selection module 906 selects or otherwise identifies the matched filter in the filter table 902 that is associated current delivery mode and/or current delivery configuration and also associated with the respective sensing arrangement 830, 840, 850 whose output is being maintained by the sensor output buffer 904. The filter selection module 906 is coupled to the filtering module 908 to provide the filter coefficient values for the selected matched filter to the filtering module 908. Additionally, the filter selection module 906 is coupled to the comparison module 910 to provide the one or more threshold values associated with the selected matched filter to the comparison module 910 for use in detecting or otherwise identifying the condition of interest associated with the selected filter.

The filtering module 908 generally represents the component of the detection module 900 that is coupled to the sensor output buffer 904 to obtain the recent output from the respective sensing arrangement 830, 840, 850 and apply the selected matched filter to the recent output using the filter coefficient values received from the filter selection module 906. In exemplary embodiments, the selected matched filter is a finite impulse response (FIR) filter, so that to apply the selected matched filter, the filtering module 908 calculates or otherwise determines a weighted sum of recently sampled output values from the respective sensing arrangement 830, 840, 850 using the weighting indicated by the filter coefficient values. As described in greater detail below, the filter coefficient values correspond to an expected output of the respective sensing arrangement 830, 840, 850 when the associated condition of interest exists within or is otherwise exhibited by the infusion device 802 and/or the fluid delivery path. Thus, applying the matched filter to the recently sampled output values effectively performs a convolution operation on the recently sampled output with the expected output when the condition exists within the infusion device 802 and/or the fluid delivery path. The filtered output of the sensing arrangement 830, 840, 850 corresponds to the weighted sum determined by the filtering module 908, which, in turn, is provided to the comparison module 910.

It should be noted that in some alternative embodiments, the filtering module 908 may not provide a filtered output value to the comparison module 910 until the number of sensor output values maintained in the sensor output buffer 904 is greater than or equal to the number of filter coefficient values for the matched filter to ensure that the filtered output has settled. For example, in one or more exemplary embodiments, the sum of the filter coefficient values is equal to zero, so that the integral (or net area under the curve) for the filter impulse response is equal to zero and the filtered output converges to or otherwise settles at or around zero value in the absence of the condition being detected once the number of sensor output values equals the number of filter coefficient values. In other embodiments, the filtering module 908 may not provide a filtered output value to the comparison module 910 until the sensor output values maintained in the sensor output buffer 904 correspond to a number of increments of a analysis domain variable that ensures the filtered output has settled, wherein the filtering module 908 interpolates the sensor output values to the increments of the analysis domain variable and provides a number of sensor output values equal to the number of filter coefficient values before applying the filter.

The comparison module 910 generally represents the component of the detection module 900 that is coupled to the output of the filtering module 908 and compares the filtered output provided by the filtering module 908 to the one or more threshold values associated with the selected matched filter that were provided by the filter selection module 906. In this regard, when a magnitude of the filtered output is greater than (or alternatively, is less than) a threshold value provided by the filter selection module 906, the comparison module 910 detects or otherwise identifies the occurrence of the condition of interest associated with the selected matched filter and/or that threshold value and generates or otherwise provides an output signal indicative of the occurrence of the condition of interest. For example, when the filtered output of the force sensing arrangement 840 is greater than an occlusion threshold force value provided by the filter selection module 906, the comparison module 910 detects or otherwise identifies the occurrence of a potential occlusion condition and generates or otherwise provides an output signal indicative of the occlusion condition to the pump control system 820 and/or control module 804. In alternative embodiments, the comparison module 910 may detect or otherwise identify the occurrence of the condition of interest associated with the selected matched filter when a slope of the filtered output is greater than (or alternatively, is less than) a threshold value provided by the filter selection module 906. As described in greater detail below, in response to an indication that an occlusion condition or some other anomalous condition has been detected, the pump control system 820 and/or control module 804 may initiate one or more remedial actions to prevent inadvertent underdelivery and/or overdelivery of fluid to the user or otherwise mitigate the detected condition.

In some embodiments, the comparison module 910 also receives the most recently obtained output of the respective sensing arrangement 830, 840, 850 and detects or otherwise identifies a condition of interest when the unfiltered output of the respective sensing arrangement 830, 840, 850 is greater than (or less than) an absolute threshold value. For example, the comparison module 910 may receive the most recent force measurement from the force sensing arrangement 840 and detect or otherwise identify an occlusion condition when the most recent force measurement is greater than an upper occlusion threshold force value that provides a margin that accounts for noise, manufacturing variations, component tolerances, and/or other factors to avoid or otherwise limit the frequency and/or amount of false positives. In this regard, the absolute threshold value comparison may function as a failsafe that ensures the potential occurrence of a particular condition, such as an occlusion condition, is always identified in certain circumstances.

Figure 10:
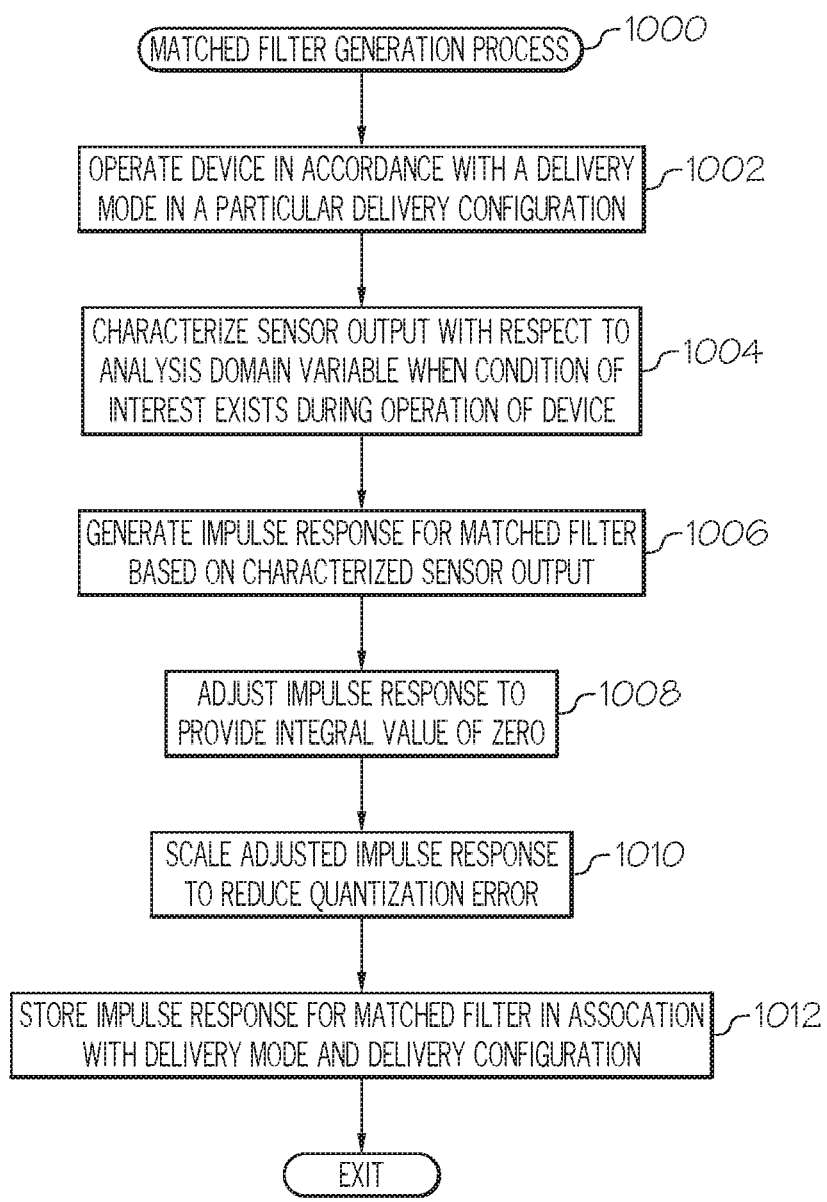
FIG. 10 is a flow diagram of an exemplary matched filter generation process suitable for use with the control system of FIG. 8 to generate an impulse response of a matched filter capable of being utilized to detect a condition of interest in accordance with one or more exemplary embodiments.

FIG. 10 depicts an exemplary matched filter generation process 1000 for generating a matched filter suitable for use in detecting a condition of interest based on the output of a sensing arrangement associated with an infusion device. The various tasks performed in connection with the matched filter generation process 1000 may be performed by hardware, firmware, software, or any combination thereof. For illustrative purposes, the following description refers to elements mentioned above in connection with FIGS. 1-9. It should be appreciated that the matched filter generation process 1000 may include any number of additional or alternative tasks, the tasks need not be performed in the illustrated order and/or the tasks may be performed concurrently, and/or the matched filter generation process 1000 may be incorporated into a more comprehensive procedure or process having additional functionality not described in detail herein. Moreover, one or more of the tasks shown and described in the context of FIG. 10 could be omitted from a practical embodiment of the matched filter generation process 1000 as long as the intended overall functionality remains intact.

In exemplary embodiments, the matched filter generation process 1000 begins by operating an infusion device in accordance with a particular delivery mode in a particular delivery configuration and characterizing the output of the sensing arrangement to be utilized to detect a condition of interest when that condition of interest is occurring within the infusion device and/or the fluid delivery path (tasks 1002, 1004). In this regard, the condition to be detected is simulated or otherwise caused to occur within the infusion device and/or the fluid delivery path while the infusion device is being operated to simulate delivery of fluid from the reservoir to a user. For example, an occlusion condition may be simulated by blocking or otherwise obstructing the fluid delivery path, for example, by clamping or pinching the tubing of an infusion set coupled to the infusion device and/or the fluid delivery port of the reservoir. Similarly, a leakage condition may be simulated by inserting or otherwise providing a reservoir known to be exhibiting a leak into the infusion device, or alternatively, coupling an infusion set known to be exhibiting a leak to the reservoir in the infusion device. While the condition of interest is being exhibited, dosage commands are provided to the control module 804 to operate the motor 232, 810 of the infusion device 200, 802 to simulate delivery of fluid to the user via the fluid delivery path in accordance with a particular delivery mode. For example, dosage commands may be provided to the control module 804 to operate the motor 232, 810 in a manner that simulates a basal rate of delivery or a bolus rate of delivery to a user.

While the motor 232, 810 of the infusion device 200, 802 is operated to simulate delivery of fluid to a user, the output of a respective sensing arrangement 830, 840, 850 is sampled, obtained, or otherwise monitored with respect to a particular analysis domain variable to characterize the output of the respective sensing arrangement 830, 840, 850 by correlating the output value from the respective sensing arrangement 830, 840, 850 to the analysis domain variable. For example, while the motor 232, 810 is operated to simulate delivery while an occlusion condition is simulated, the output of the force sensing arrangement 440, 840 is sampled and those force measurements are correlated to an analysis domain variable, such as, for example, the number of motor steps during the delivery, number of units delivered during the delivery, the duration of time for the delivery, or the like. In this regard, the values for the analysis domain variable may be obtained from another sensing arrangement associated with the infusion device 200, 802, such as, for example, the motor sensing arrangement 812, a volume sensing arrangement 850, or the like. In some embodiments, the sensor output values may be interpolated to correlate the sensor output values to increments of the analysis domain variable when sensor output values are not obtained for each incremental change in the analysis domain variable. For example, force measurements may be obtained from the force sensing arrangement 840 before and/or after each operation of the motor 810 in accordance with a motor command. Accordingly, the force measurements may be interpolated using the force measurements obtained before and after operation of the motor to estimate force measurement values for each incremental motor step during operation of the motor. For example, if the motor 810 is operated to provide two steps of rotation, the midpoint between a first force sensor measurement obtained before the two steps of rotation and a second force sensor measurement obtained after the two steps of rotation may be correlated to one step of rotation from the preceding motor position. In exemplary embodiments, operation of the infusion device 200, 802 while the condition of interest is simulated and characterization of the resulting sensor output is performed multiple times so that the correlation between the sensor output values and the analysis domain variable is averaged over multiple operations of the infusion device 200, 802, for example, by performing linear regression.

In exemplary embodiments, after characterizing the output of a sensing arrangement with respect to an analysis domain variable, the matched filter generation process 1000 continues by generating an impulse response for the matched filter that matches or otherwise corresponds to the characterized sensor output (task 1006). In this regard, filter coefficient values are generated for the matched filter that match or otherwise correspond to the relationship between the characterized sensor output and the analysis domain variable, such that the impulse response for the matched filter corresponds to a convolved version of the characterized sensor output with respect to the analysis domain variable. For example, where the analysis domain variable corresponds to the x-axis, the filter coefficient values may provide a slope corresponding to a y-axis reflection of the characterized sensor output with respect to the analysis domain variable.

Figure 11:
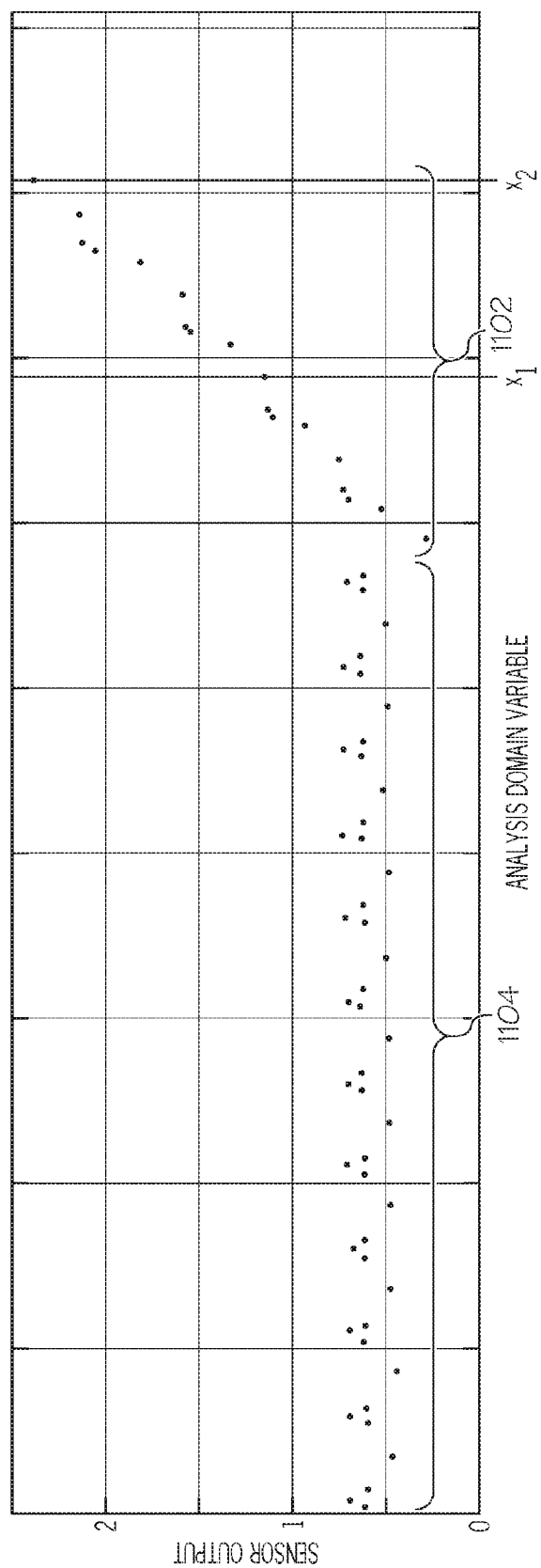
FIG. 11 is a graph depicting an exemplary relationship between the output of a sensing arrangement in the control system of FIG. 8 with respect to an analysis domain variable when a condition of interest to be detected exists.
Figure 12:
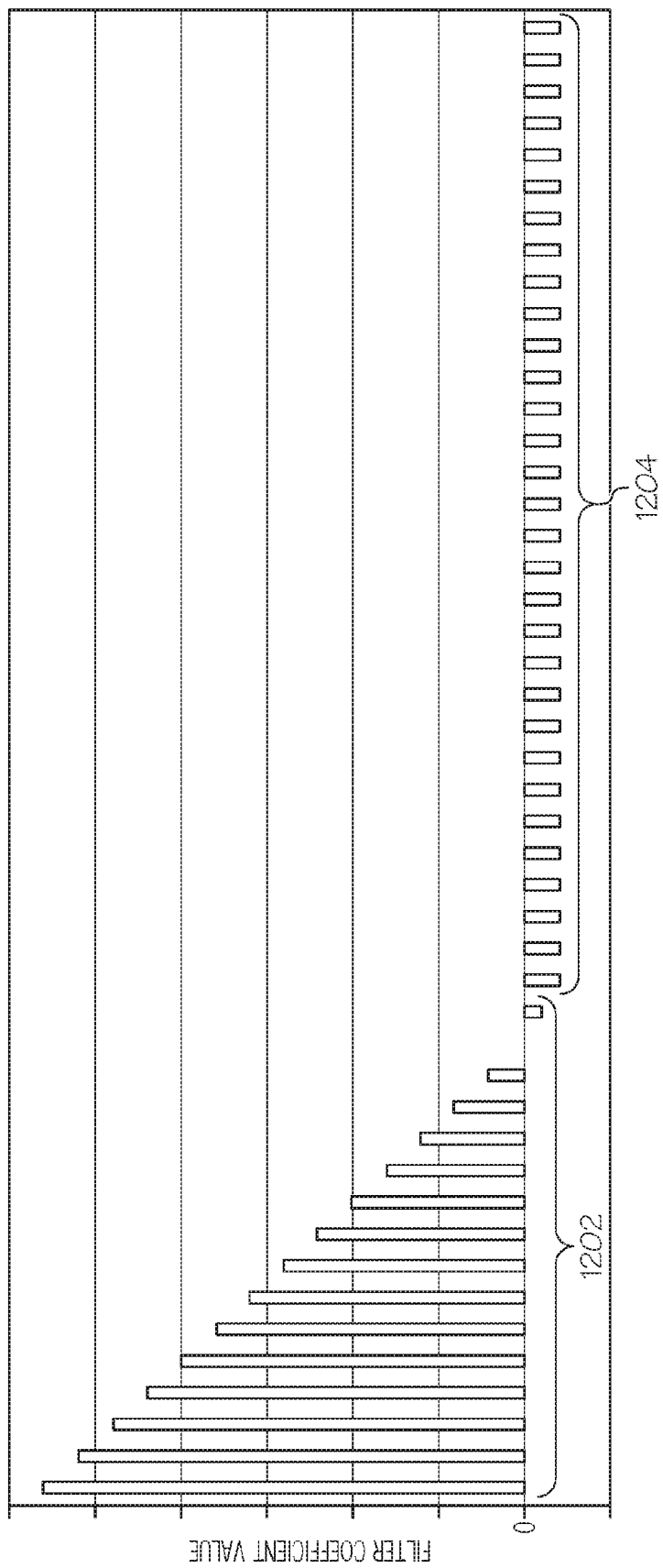
FIG. 12 is a graph depicting an exemplary impulse response for a matched filter suitable for use in detecting the condition of interest that may be generated based on the relationship between the output of the sensing arrangement and the analysis domain variable of FIG. 11 in accordance with one exemplary embodiment of the matched filter generation process of FIG. 10.

FIG. 11 depicts a graph of a sensor output with respect to analysis domain variable and FIG. 12 depicts a graph of filter coefficient values for a matched filter that corresponds to the relationship between the sensor output and the analysis domain variable of FIG. 11. In exemplary embodiments, the sensor output in FIG. 11 corresponds to the output of a force sensing arrangement 440, 840 in response to an occlusion condition with respect to motor steps of rotation of the rotor 402 of the motor 232, 810 as the analysis domain variable. However, as noted above, the subject matter described herein is not limited to detecting occlusion conditions using a force sensing arrangement. As illustrated, the matched filter includes a first set 1202 of filter coefficient values configured to provide a slope that is substantially equal to the negative slope of the sensor output with respect to the analysis domain variable over a range 1102 of the analysis domain variable that corresponds to the occurrence of the condition of interest. For example, the range 1102 of the analysis domain variable may correspond to the force measurement values obtained from the force sensing arrangement 440, 840 when an occlusion condition exists or is otherwise being simulated, wherein the first set 1202 of filter coefficient values are chosen to provide a slope substantially equal to the negative of the force measurement values with respect to the analysis domain variable for the range 1102.

Still referring to FIG. 10, and with continued reference to FIGS. 11-12, in exemplary embodiments, the matched filter generation process 1000 continues by adjusting the impulse response of the matched filter to provide an integral value (or net area under the curve) equal to zero (task 1008). In accordance with one or more embodiments, the matched filter includes a second set 1204 of filter coefficient values chosen to cancel the first set 1202 of filter coefficient values such that the sum of the filter coefficient values is equal to zero. In this regard, the number of filter coefficient values in the second set 1204 may be chosen to vary the sensitivity or responsiveness of the filtered output from the matched filter to changes in the output of the sensing arrangement. For example, reducing the number of filter coefficient values in the second set 1204 increases the responsiveness of the filtered output with respect to the sensor output while also increasing the frequency or likelihood of false positives (e.g., occlusion conditions being detected in response to noise superimposed on the sensor output when no occlusion in the fluid path exists). Conversely, increasing the number of filter coefficient values in the second set 1204 decreases the responsiveness of the filtered output with respect to the sensor output but also decreases the frequency or likelihood of false positives. In the illustrated embodiment of FIG. 12, the filter coefficient values in the second set 1204 are constant and equal to one another. In other embodiments, the second set 1204 of filter coefficient values may be chosen to provide a slope equal to the negative of the force measurement values with respect to the analysis domain variable for a range 1104 of the analysis domain variable corresponding to steady-state operation of the infusion device in the absence of an occlusion condition.

Referring again to FIG. 10, in exemplary embodiments, the matched filter generation process 1000 continues by scaling the adjusted impulse response for the matched filter to reduce quantization error when applying the matched filter to the sensor output (task 1010). In this regard, the second set 1204 of filter coefficient values are scaled in a manner that reduces the quantization error could result from the inclusion of the second set 1204 of filter coefficient values in the matched filter. For example, if the second set 1204 of filter coefficient values includes a plurality of filter coefficient values having an equal (or constant) value, both sets 1202, 1204 of the filter coefficient values may be scaled (e.g., by multiplying them by a scaling factor) to provide integer values for the second set 1204 of filter coefficient values. In exemplary embodiments, the integer values are chosen to be a power of two. For example, if the constant filter coefficient values for the second set 1204 are equal to 0.5, both sets 1202, 1204 of the filter coefficient values may be scaled by a factor of four so that the constant filter coefficient values for the second set 1204 are equal to two. As a result, for some processing architectures, quantization errors associated with the second set 1204 of values are reduced and/or the performance is improved when applying the matched filter (e.g., by leveraging bit shifting or other similar techniques to accomplish multiplication by the second set 1204 of values).

In exemplary embodiments, after the impulse response for the matched filter is adjusted to provide an integral value of zero and scaled to reduce quantization error, the matched filter generation process 1000 stores or otherwise maintains the impulse response for the matched filter in association with the delivery configuration and the delivery mode used to obtain the sensor output for generating that filter (task 1012). As described above, the filter table 902 stores or otherwise maintains the sets 1202, 1204 of coefficient values for the matched filter in association with information identifying the delivery configuration for the infusion device 200, 802 when the infusion device 200, 802 was operated to obtain the sensor output values used to generate the filter along with information identifying the delivery mode in which the infusion device 200, 802 was operated. Additionally, the filter table 902 may maintain, in association with the matched filter, information identifying the sensing arrangement associated with the matched filter, information identifying the condition of interest that is detectable using the matched filter, and/or information identifying the analysis domain variable utilized for the matched filter.

Figure 13:
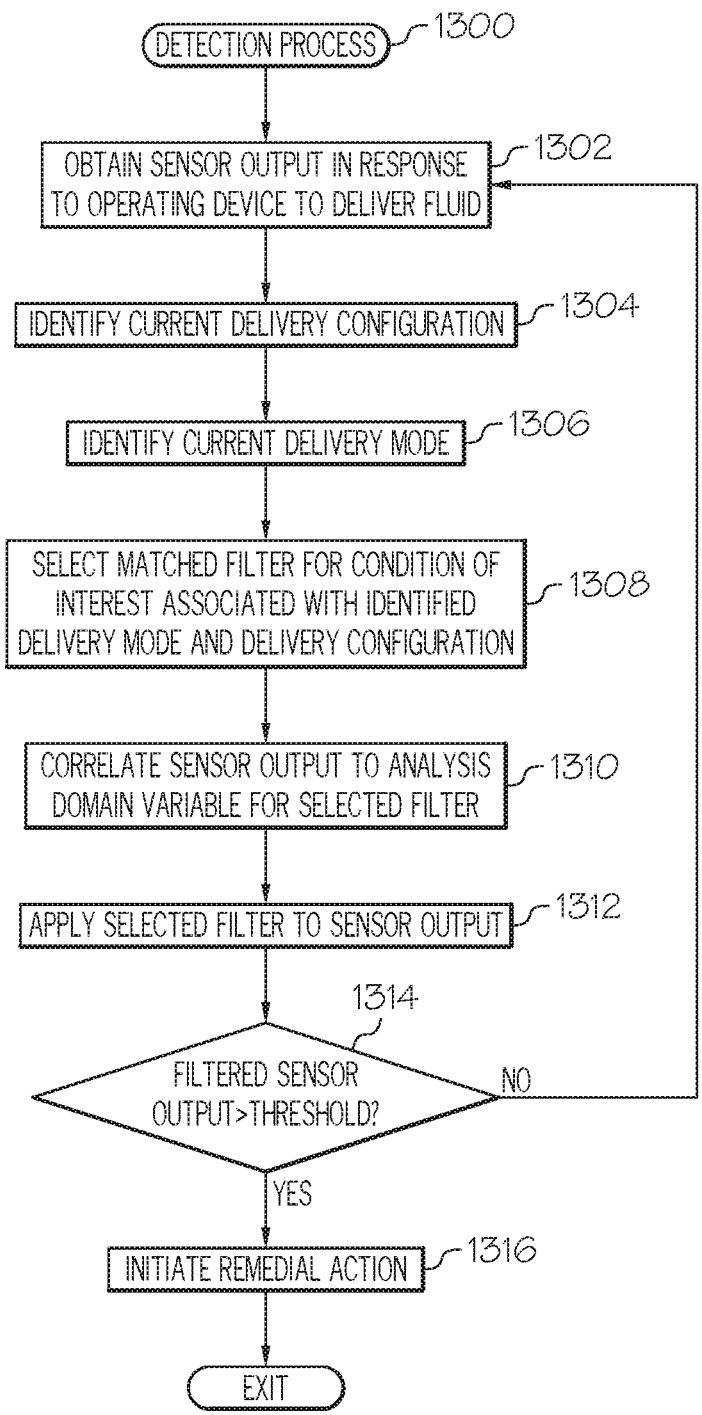
FIG. 13 is a flow diagram of an exemplary detection process suitable for use with the control system of FIG. 8 to detect a condition of interest using a matched filter in accordance with one or more exemplary embodiments.

FIG. 13 depicts an exemplary detection process 1300 suitable for implementation by an infusion device to detecting a condition of interest based on the output of a sensing arrangement associated with an infusion device. The various tasks performed in connection with the detection process 1300 may be performed by hardware, firmware, software, or any combination thereof. For illustrative purposes, the following description refers to elements mentioned above in connection with FIGS. 1-9. In practice, portions of the detection process 1300 may be performed by different elements of an infusion device 200, 802, such as, for example, the control module 804, the pump control system 820, the sensing arrangements 830, 840, 850, the detection module 900, the filter table 902, the sensor output buffer 904, the filter selection module 906, the filtering module 908, and/or the comparison module 910. It should be appreciated that the detection process 1300 may include any number of additional or alternative tasks, the tasks need not be performed in the illustrated order and/or the tasks may be performed concurrently, and/or the detection process 1300 may be incorporated into a more comprehensive procedure or process having additional functionality not described in detail herein. Moreover, one or more of the tasks shown and described in the context of FIG. 13 could be omitted from a practical embodiment of the detection process 1300 as long as the intended overall functionality remains intact.

In exemplary embodiments, the detection process 1300 receives or otherwise obtains output from a sensing arrangement corresponding to a characteristic influenced by operation of the infusion device in response to operating the infusion device to deliver fluid to a user (task 1302). For example, after the control module 804 operates the motor driver module 808 to rotate the rotor 402 of the motor 232, 810 by a commanded number of motor steps to displace the plunger 222, 822 in a reservoir 206, 816 in a delivery direction 250 by an amount of displacement corresponding to a desired dosage, the control module 804 and/or the sensor output buffer 904 may sample or otherwise obtain a measured value for the reactionary force exerted by the plunger 222, 822 from the force sensing arrangement 440, 840.

The illustrated detection process 1300 continues by identifying the current delivery configuration for the infusion device, identifying the current delivery mode for the infusion device, and selecting a matched filter to be applied to the obtained sensor output based on the current delivery configuration and the current delivery mode (tasks 1304, 1306, 1308). The control module 804 and/or the filter selection module 906 obtains (e.g., from the pump control system 820) information identifying the type of infusion set 824 and/or the length of tubing coupled to the infusion device 200, 802, information identifying the type and/or size of reservoir 206, 816 inserted in the infusion device 200, 802, and/or any other information indicative of an aspect of the physical configuration of the infusion device 200, 802 that is capable of influencing the characteristic sensed by the sensing arrangement. Additionally, the control module 804 and/or the filter selection module 906 obtains (e.g., from the pump control system 820) information identifying the current delivery mode and/or fluid delivery rate for the infusion device 200, 802. For example, depending on the time of day, the infusion device 200, 802 may be operated in a basal delivery mode (e.g., overnight) to provide a basal rate of delivery of fluid from the reservoir 206, 816, a bolus delivery mode (e.g., around mealtime) to provide a bolus rate of delivery of fluid from the reservoir 206, 816, or a custom delivery mode to provide some other customized or user-configured rate of delivery of fluid from the reservoir 206, 826. Additionally, in some embodiments, there may be multiple bolus delivery modes and/or basal delivery modes with different rates of delivery associated therewith. Accordingly, in some embodiments, the matched filters may be associated with a particular delivery rate (or range thereof) for application to the one or more delivery modes that provide that delivery rate (or a delivery rate within the associated range).

Based on the current delivery mode for the infusion device 200, 802 and the current delivery configuration of the infusion device 200, 802, the control module 804 and/or the filter selection module 906 selects or otherwise identifies the matched filter in the filter table 902 associated with the current delivery configuration and current delivery mode for the sensing arrangement and the condition of interest. For example, when the condition of interest is an occlusion condition, the control module 804 and/or the filter selection module 906 may select the matched filter in the filter table 902 associated with the force sensing arrangement 440, 840, an occlusion condition, the current delivery configuration, and the current delivery mode.

In exemplary embodiments, the detection process 1300 continues by correlating the obtained sensor output to the analysis domain variable associated with the selected matched filter and applying the selected matched filter to the correlated sensor output (tasks 1310, 1312). As described above, when the sensor output values are not obtained for each incremental change in the analysis domain variable, the obtained sensor output values are interpolated to obtain estimated sensor output values for the intermediate analysis domain variable increments between analysis domain variable values corresponding to the obtained sensor output values. For example, when the analysis domain variable is a number of motor steps, the control module 804 and/or the filtering module 908 may interpolate force measurements obtained from the force sensing arrangement 840 before and/or after operating the motor 810 to estimate force measurement values for each incremental motor step during that operation of the motor. After correlating the obtained sensor output to the analysis domain variable, the detection process 1300 continues by applying the filter coefficient values for the selected matched filter to the correlated sensor output values to obtain the filtered output. As described above, the control module 804 and/or the filtering module 908 applies the selected matched filter by calculating or otherwise determining a weighted sum of the recent sensor output values using the filter coefficient values as the weighting factors for the respective sensor output values.

In exemplary embodiments, after applying the selected matched filter to the sensor output, the detection process 1300 continues by determining whether the filtered sensor output is greater than (or less than) a threshold value for the condition of interest and initiating a remedial action when the filtered sensor output is greater than the threshold value (tasks 1314, 1316). As described above, the control module 804 and/or the filtering module 908 detects or otherwise identifies the occurrence of the condition of interest when the filtered sensor output exceeds the threshold value provided by the filter selection module 906 from the filter table 902. In this regard, when the filtered sensor output is greater than the threshold value, the control module 804 and/or the filtering module 908 may generate or otherwise provide an indication of the condition of interest to the pump control system 820 or another supervisory system. For example, when the filtered force measurement from the force sensing arrangement 440, 840 exceeds an occlusion threshold force value, the control module 804 and/or the filtering module 908 may generate or otherwise provide an indication of an occlusion condition to the pump control system 820. In response to the indication of the occlusion condition, the pump control system 820 may notify the user (e.g., by generating a visual and/or auditory notification on the CCD 106 and/or computer 108) or initiate another remedial action to address the potential occlusion condition.

As illustrated, the loop defined by tasks 1302, 1304, 1306, 1308, 1310, 1312 and 1314 may repeat indefinitely throughout operation of a fluid infusion device 200, 802 to continually monitor the output of one or more sensing arrangements 830, 840 associated with the infusion device 200, 802. In this regard, as the delivery mode and/or delivery configuration of the infusion device 200, 802 changes over time, the control module 804 and/or the filter selection module 906 may dynamically select the appropriate matched filter for the current delivery mode and delivery configuration of the infusion device 200, 802. For example, if operation of the infusion device 200, 802 changes from a basal delivery mode (or basal delivery rate) to bolus delivery mode (or bolus delivery rate), the control module 804 and/or the filter selection module 906 may select the matched filter for detecting an occlusion condition using the force sensing arrangement 440, 840 that is associated with the bolus delivery mode to more accurately and/or reliably detect a potential occlusion condition while the infusion device 200, 802 is operated in the bolus delivery mode rather than utilizing a matched filter configured for the basal delivery mode. In this manner, the detection process 1300 is adaptive to conform to the current delivery status of the infusion device 200, 802.

Figure 14:
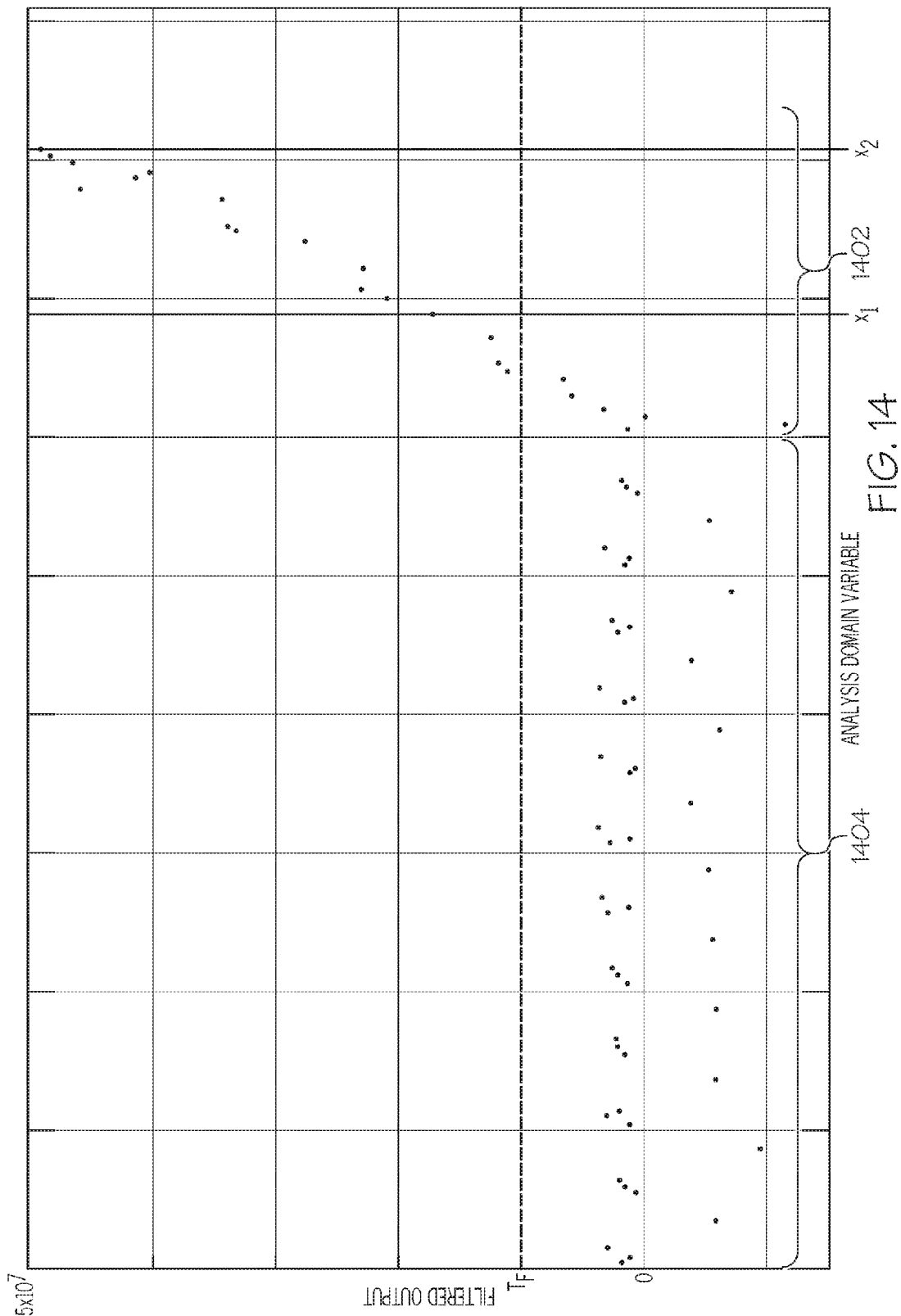
FIG. 14 is a graph depicting an exemplary relationship between a filtered output obtained by applying the matched filter of FIG. 12 to the sensor output of FIG. 11 with respect to the analysis domain variable in accordance with one or more exemplary embodiments.

FIG. 14 depicts a graph of a filtered sensor output when the matched filter of FIG. 12 is applied to the sensor output of FIG. 11. As illustrated, by virtue of the integral of the matched filter being equal to zero, the filtered sensor output oscillates about zero, and thus, is substantially equal to zero over the range 1104 of the analysis domain variable while the output of the force sensing arrangement 440, 840 is substantially constant. At the same time, by virtue of the matched filter corresponding to a convolved version of the output of the force sensing arrangement 440, 840, the filtered output rapidly increases over the range 1102 of the analysis domain variable during which the output of the force sensing arrangement 440, 840 begins increasing in response to the occlusion condition. Thus, the occlusion threshold value used with the matched filter may be chosen so that the occlusion condition is more rapidly detected based on the filtered output relative to when the occlusion would be detected based on the unfiltered sensor output. For example, the occlusion threshold value ($T_F$) for use with the filtered output may be chosen such that the occlusion condition is detected at analysis domain variable increment ($x_1$) when the filtered output exceeds the occlusion threshold value ($T_F$) for at least 4 successive analysis domain variable increments, while the occlusion condition would not be detected until analysis domain variable increment ($x_2$) based on the unfiltered sensor output.

To briefly summarize, the relatively high signal-to-noise ratio provided by the matched filter may allow a lower threshold value to be utilized, which, in combination with the rapid increase in the filtered output exhibited in response to the condition of interest, decreases the amount of time (or delay) required for the filtered output to exceed the threshold value. Accordingly, incipient occlusion conditions or other anomalous conditions may be detected and corresponding remedial actions initiated with reduced delay, thereby mitigating the impact of such anomalous conditions on the user. It should be noted that multiple matched filters with varying lengths may be used concurrently to achieve a desired level of reliability and response time. For example, a condition of interest may be detected when the filtered output from a relatively shorter length matched filter (e.g., 64 coefficients) exceeds a first threshold value while the filtered output from a relatively longer length matched filter (e.g., 256 coefficients) also exceeds a second threshold value at the same time. It will be appreciated that numerous possible detection schemes exist, and the subject matter described herein is not limited to any particular manner in which a condition of interest is detected or otherwise declared.

The foregoing description may refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically. In addition, certain terminology may also be used in the herein for the purpose of reference only, and thus is not intended to be limiting. For example, terms such as "first", "second", and other such numerical terms referring to structures do not imply a sequence or order unless clearly indicated by the context.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of detecting a condition associated with operation of a fluid infusion device, the method comprising:
    obtaining an output indicative of a characteristic influenced by the operation of a fluid infusion device from a sensing arrangement;
    interpolating the output of the sensing arrangement to obtain correlated output values comprising estimated output values for intermediate values of an analysis domain variable between analysis domain variable values corresponding to the output, wherein the analysis domain variable is associated with a matched filter corresponding to the condition;
    applying the matched filter to the correlated output values to calculate a filtered output as a weighted sum of the respective correlated output values using filter coefficient values of the matched filter as weighting factors for the respective correlated output values; and
    detecting the condition based on the filtered output.

2. The method of claim 1, further comprising:
    identifying a current physical configuration of the fluid infusion device; and selecting the matched filter associated with the current physical configuration.

3. The method of claim 1, further comprising:
identifying a current operating mode for the fluid infusion device; and
selecting the matched filter associated with the current operating mode.

4. The method of claim 1, the fluid infusion device includes a motor operable to displace a plunger of a reservoir to deliver fluid to a user, wherein the output is influenced by displacement of the plunger.

5. The method of claim 4, wherein:
obtaining the output comprises obtaining a force measurement output indicative of a force opposing the displacement of the plunger from a force sensing arrangement;
applying the matched filter comprises applying the matched filter corresponding to an occlusion condition to the force measurement output, resulting in a filtered force measurement; and
detecting the condition comprises detecting the occlusion condition when a magnitude of the filtered force measurement is greater than an occlusion force threshold.

6. The method of claim 4, wherein:
obtaining the output comprises obtaining a volume measurement output indicative of a remaining volume of fluid in the reservoir from a volume sensing arrangement;
applying the matched filter comprises applying the matched filter corresponding to a leakage condition to the volume measurement output, resulting in a filtered volume measurement; and
detecting the condition comprises detecting the leakage condition based on the filtered volume measurement.

7. The method of claim 1, wherein detecting the condition based on the filtered output comprises detecting the condition based on the weighted sum.

8. The method of claim 1, the filter coefficient values comprising a first set of values corresponding to an expected output from the sensing arrangement in response to the condition and a second set of values to cancel the first set of values such that an integral of the matched filter is equal to zero, wherein the method further comprises scaling the first set of values and the second set of values so that the second set of values comprise integer values equal to a power of two.

9. The method of claim 1, the analysis domain variable comprising a number of motor steps and the output comprising force measurements obtained before and after an operation of a motor, wherein interpolating the output comprises interpolating the force measurements to estimate force measurement values for each incremental motor step during the operation of the motor.

10. A method of detecting an occlusion condition associated with operation of a fluid infusion device including a motor operable to displace a plunger of a reservoir to deliver fluid, the method comprising:
obtaining a force measurement output indicative of a force opposing displacement of the plunger from a force sensing arrangement;
interpolating the force measurement output to obtain correlated force measurements comprising estimated force measurement values for intermediate values of motor steps between respective motor steps corresponding to the force measurement output, resulting in correlated force measurements;
applying a matched filter corresponding to the occlusion condition to the correlated force measurements to calculate a filtered force measurement as a weighted sum of the respective correlated force measurements using filter coefficient values of the matched filter as weighting factors for the respective correlated force measurements; and
detecting the occlusion condition based on the filtered force measurement.

11. The method of claim 10, further comprising:
identifying a current physical configuration of the fluid infusion device; and
selecting the matched filter associated with the current physical configuration.

12. The method of claim 10, further comprising:
identifying a current operating mode for the fluid infusion device; and
selecting the matched filter associated with the current operating mode.

13. The method of claim 10, wherein interpolating the force measurement output comprises interpolating force measurements to estimate force measurement values for each incremental motor step during the operation of the motor.

14. The method of claim 10, wherein detecting the occlusion condition comprises detecting the occlusion condition when a magnitude of the filtered force measurement is greater than an occlusion force threshold.

15. A method of detecting a leakage condition associated with operation of a fluid infusion device including a motor operable to displace a plunger of a reservoir to deliver fluid, the method comprising:
obtaining a volume measurement output indicative of a remaining volume of fluid in the reservoir from a volume sensing arrangement;
interpolating the volume measurement output to obtain correlated volume measurements comprising estimated volume measurement values for intermediate values of motor steps between respective motor steps corresponding to the volume measurement output, resulting in correlated volume measurements;
applying a matched filter corresponding to the leakage condition to the correlated volume measurements to calculate a filtered volume measurement as a weighted sum of the respective correlated volume measurements using filter coefficient values of the matched filter as weighting factors for the respective correlated volume measurements; and
detecting the leakage condition based on the filtered volume measurement.

16. The method of claim 15, further comprising:
identifying a current physical configuration of the fluid infusion device; and
selecting the matched filter associated with the current physical configuration.

17. The method of claim 15, further comprising:
identifying a current operating mode for the fluid infusion device; and
selecting the matched filter associated with the current operating mode.

18. The method of claim 15, wherein interpolating the volume measurement output comprises interpolating volume measurements to estimate volume measurement values for each incremental motor step during the operation of the motor.

* * * * *